US012757948B2

(12) United States Patent
Schlam

(10) Patent No.: US 12,757,948 B2
(45) Date of Patent: Oct. 13, 2026

(54) WEARABLE COOLING SYSTEM FOR BODY COOLING AND METHOD FOR FABRICATING THE WEARABLE COOLING SYSTEM

(71) Applicant: Omius Inc., Monterrey (MX)

(72) Inventor: Gustavo Cadena Schlam, Veracruz (MX)

(73) Assignee: Omius Inc. (MX)

( * ) Notice: Subject to any disclaimer, the term of this patent is extended or adjusted under 35 U.S.C. 154(b) by 196 days.

(21) Appl. No.: 18/598,611

(22) Filed: Mar. 7, 2024

(65) Prior Publication Data

US 2024/0285013 A1 Aug. 29, 2024

Related U.S. Application Data

(63) Continuation-in-part of application No. 18/124,283, filed on Mar. 21, 2023, now Pat. No. 12,239,178, (Continued)

(51) Int. Cl.
*A41D 20/00* (2006.01)
*A41D 13/005* (2006.01)
(Continued)

(52) U.S. Cl.
CPC ..... *A41D 13/0056* (2013.01); *A41D 13/0053* (2013.01); *A41D 20/005* (2013.01); (Continued)

(58) Field of Classification Search
None
See application file for complete search history.

(56) References Cited

U.S. PATENT DOCUMENTS 2,875,447 A 3/1959 Goldmerstein
4,130,902 A * 12/1978 Mackenroth, III ...... A42C 5/02 2/171.2
(Continued)

FOREIGN PATENT DOCUMENTS

CA 2135966 A1 * 5/1996 .............. A61F 7/10
CN 102351494 A 2/2012
(Continued)

OTHER PUBLICATIONS

Almajali, Engineered carbon foam for temperature control applications, May 2010 (Year: 2010).
(Continued)

*Primary Examiner* — Jeffrey A Vonch
(74) *Attorney, Agent, or Firm* — Run8 Patent Group, LLC; Peter Miller; Leah Raddatz

(57) ABSTRACT

One variation of a system includes a garment insert: configured to be worn across a dermal surface; including a textile panel defining a grid receptacle; and including a grid structure arranged within the grid receptacle and defining an array of apertures. The system further includes a cooling unit including a heatsink structure: defining a base section defining an inner surface configured to contact the dermal surface; and defining a set of heatsink columns extending from the base section, opposite the inner surface, and configured to seat extending through the array of apertures. The cooling unit: is configured to wick moisture from the dermal surface toward surfaces of the set of heatsink columns; and includes a polymer frame, bonded to the heatsink structure about the base section, configured to abut surfaces of the base section to surfaces of the grid receptacle to flexibly retain the cooling unit within the grid receptacle.

20 Claims, 10 Drawing Sheets

Related U.S. Application Data which is a continuation of application No. 17/037,457, filed on Sep. 29, 2020, now Pat. No. 11,632,996, which is a continuation of application No. 16/574,048, filed on Sep. 17, 2019, now Pat. No. 10,820,652.

(60) Provisional application No. 63/450,549, filed on Mar. 7, 2023, provisional application No. 62/732,193, filed on Sep. 17, 2018.

(51) Int. Cl.

| | |
|---|---|
| ***A42B 1/008*** | (2021.01) |
| ***A61F 7/00*** | (2006.01) |
| ***B32B 3/10*** | (2006.01) |
| ***B32B 3/24*** | (2006.01) |
| ***B32B 5/02*** | (2006.01) |
| ***B32B 7/06*** | (2019.01) |
| ***B32B 27/12*** | (2006.01) |
| ***B32B 27/28*** | (2006.01) |
| ***B32B 27/36*** | (2006.01) |
| *A41D 1/04* | (2006.01) |
| *B05D 3/00* | (2006.01) |
| *B05D 3/02* | (2006.01) |
| *B05D 3/04* | (2006.01) |
| *B05D 3/10* | (2006.01) |
| *B23P 15/26* | (2006.01) |
| *B32B 3/26* | (2006.01) |
| *C04B 28/00* | (2006.01) |
| *C04B 28/18* | (2006.01) |
| *F28D 21/00* | (2006.01) |
| *F28F 13/00* | (2006.01) |
| *F28F 13/18* | (2006.01) |

(52) U.S. Cl.

CPC ................ *A42B 1/008* (2013.01); *A61F 7/00* (2013.01); *B32B 5/02* (2013.01); *B32B 7/06* (2013.01); *B32B 27/12* (2013.01); *B32B 27/283* (2013.01); *A41D 1/04* (2013.01); *A41D 13/0058* (2013.01); *A41D 2300/20* (2013.01); *A61F 2007/0001* (2013.01); *A61F 2007/0007* (2013.01); *A61F 2007/0018* (2013.01); *A61F 2007/0034* (2013.01); *A61F 2007/0098* (2013.01); *B05D 3/002* (2013.01); *B05D 3/007* (2013.01); *B05D 3/0254* (2013.01); *B05D 3/0453* (2013.01); *B05D 3/107* (2013.01); *B05D 3/108* (2013.01); *B05D 2203/30* (2013.01); *B23P 15/26* (2013.01); *B32B 3/10* (2013.01); *B32B 3/266* (2013.01); *B32B 27/36* (2013.01); *B32B 2367/00* (2013.01); *B32B 2383/00* (2013.01); *C04B 28/005* (2013.01); *C04B 28/182* (2013.01); *F28D 2021/0029* (2013.01); *F28F 13/003* (2013.01); *F28F 13/185* (2013.01); *F28F 2245/02* (2013.01); *F28F 2260/00* (2013.01); *Y10T 428/12479* (2015.01); *Y10T 428/24008* (2015.01); *Y10T 428/24017* (2015.01); *Y10T 428/24174* (2015.01); *Y10T 428/24331* (2015.01); *Y10T 428/24339* (2015.01); *Y10T 428/2457* (2015.01); *Y10T 428/24612* (2015.01); *Y10T 428/249967* (2015.04); *Y10T 428/249968* (2015.04); *Y10T 428/249981* (2015.04)

(56) References Cited

U.S. PATENT DOCUMENTS 4,470,263 A 9/1984 Lehovec et al.
4,833,106 A 5/1989 Horie
5,256,450 A 10/1993 Catena
5,378,529 A 1/1995 Bourdeau
5,787,505 A * 8/1998 Piwko ................ A41D 13/0058 2/247
5,800,490 A * 9/1998 Patz ........................ A61F 7/007 607/108
5,802,865 A * 9/1998 Strauss ..................... A61F 7/10 62/259.3
5,970,718 A 10/1999 Arnold
6,139,787 A * 10/2000 Harrison ................. B29C 39/10 264/327
6,189,327 B1 2/2001 Strauss et al.
6,438,964 B1 * 8/2002 Giblin .................... H10N 10/13 62/3.5
6,763,671 B1 * 7/2004 Klett ......................... A61F 7/02 607/108
6,948,322 B1 9/2005 Giblin
7,048,966 B2 5/2006 Thomson
7,721,349 B1 * 5/2010 Strauss .................... A43B 3/34 450/38
8,156,570 B1 4/2012 Hockaday
8,235,096 B1 8/2012 Mahefkey et al.
8,397,518 B1 3/2013 Vistakula
9,301,557 B1 * 4/2016 Santos ...................... B32B 5/02
10,820,652 B2 * 11/2020 Schlam .............. A41D 13/0053
12,239,178 B2 * 3/2025 Schlam .............. A41D 13/0053
2002/0052569 A1 * 5/2002 Horning .................... A61F 7/10 602/41
2002/0195229 A1 12/2002 Hsieh et al.
2005/0062198 A1 * 3/2005 Pham ..................... A41D 27/08 264/259
2005/0065581 A1 * 3/2005 Fletcher .................... F28F 3/12 607/104
2005/0081277 A1 * 4/2005 Matechen .......... A41D 13/0518 2/102
2005/0092478 A1 5/2005 Jairazbhoy et al.
2007/0017814 A1 1/2007 Hwang et al.
2007/0063360 A1 3/2007 Stenkamp et al.
2007/0084587 A1 4/2007 Huang et al.
2007/0106352 A1 * 5/2007 Carstens ................... A61F 7/03 607/114
2008/0066211 A1 3/2008 Laugt et al.
2008/0154164 A1 * 6/2008 Sheehan ................... A61F 5/01 523/105
2009/0000309 A1 * 1/2009 Hershberger .......... H10N 10/13 62/3.5
2009/0049871 A1 2/2009 Klett et al.
2009/0163984 A1 * 6/2009 Robinson .................. A61F 7/02 607/114
2009/0222072 A1 * 9/2009 Robinson .................. A61F 7/02 607/114
2010/0011489 A1 1/2010 Goldmann et al.
2011/0017431 A1 1/2011 Yang et al.
2011/0034887 A1 2/2011 Forden et al.
2011/0071603 A1 * 3/2011 Moore .................... A61F 7/007 607/96
2012/0199334 A1 8/2012 Maurer et al.
2012/0211212 A1 * 8/2012 Hu .......................... F28F 21/02 428/34.1
2012/0216335 A1 8/2012 Mckenna, Jr. et al.
2013/0030341 A1 1/2013 Freer et al.
2013/0061503 A1 3/2013 Klett et al.
2013/0085552 A1 4/2013 Mandel et al.
2013/0103125 A1 * 4/2013 Radspieler ............ F28D 20/023 607/104
2014/0012161 A1 * 1/2014 Ross, Jr. ................ A41D 1/002 600/595
2014/0109282 A1 4/2014 White et al.
2014/0326287 A1 * 11/2014 Wiant .................... H10N 10/13 136/205
2015/0101788 A1 4/2015 Smith et al.
2015/0147563 A1 5/2015 Stanis et al.
2015/0173445 A1 6/2015 Gordon et al.
2015/0251335 A1 9/2015 Chapman et al.
2017/0014266 A1 1/2017 Surace et al.
2017/0023267 A1 * 1/2017 Strauss .............. A41D 13/0056
2017/0049397 A1 * 2/2017 Sun ........................ G01K 7/427

(56) References Cited

U.S. PATENT DOCUMENTS

| | | | | |
|---|---|---|---|---|
| 2018/0035728 | A1 | 2/2018 | Salas | |
| 2018/0042761 | A1* | 2/2018 | Smith | A44C 5/0007 |
| 2018/0064182 | A1* | 3/2018 | Brockway | A61F 13/085 |
| 2018/0110266 | A1* | 4/2018 | Lee | A41D 13/0025 |
| 2018/0142924 | A1 | 5/2018 | Limon | |
| 2018/0192719 | A1 | 7/2018 | Beneyto-Ferre et al. | |
| 2018/0242555 | A1* | 8/2018 | Zimmerman | A61F 7/02 |
| 2018/0263326 | A1* | 9/2018 | Ulmer | A41D 13/0053 |
| 2019/0099290 | A1* | 4/2019 | Thomas | A61F 7/08 |
| 2019/0262169 | A1* | 8/2019 | Vergara | A61F 7/0053 |
| 2020/0107601 | A1* | 4/2020 | Schlam | A41D 20/005 |
| 2020/0154808 | A1* | 5/2020 | Inouye | A42B 1/008 |
| 2020/0333079 | A1* | 10/2020 | Mcneal-Burgess | F24F 6/04 |
| 2020/0345971 | A1* | 11/2020 | Schirm | A61F 7/02 |
| 2021/0177081 | A1 | 6/2021 | Schlam et al. | |
| 2022/0249277 | A1* | 8/2022 | Hwang | A61F 7/007 |
| 2022/0287873 | A1* | 9/2022 | Taslagyan | A61F 7/007 |
| 2023/0107746 | A1* | 4/2023 | Johnston | B32B 5/26 607/112 |
| 2024/0167736 | A1* | 5/2024 | Kota | F28C 3/005 |

FOREIGN PATENT DOCUMENTS

| | | | | | |
|---|---|---|---|---|---|
| CN | 203897416 | U | * | 10/2014 | |
| CN | 105997334 | A | * | 10/2016 | A61F 7/02 |
| DE | 20014047 | U1 | * | 11/2000 | A61F 7/02 |
| FR | 613033 | A | | 11/1926 | |
| FR | 2206916 | A1 | | 6/1974 | |
| FR | 2570935 | A1 | | 4/1986 | |
| GB | 2405315 | A | * | 3/2005 | A41D 20/005 |
| JP | H05302173 | A | | 11/1993 | |
| JP | 2008195016 | A | | 8/2008 | |
| JP | 2011111643 | A | | 6/2011 | |
| JP | 2011111644 | A | | 6/2011 | |
| KR | 890004547 | Y1 | * | 7/1989 | G08B 21/06 |
| KR | 200386470 | Y1 | * | 6/2005 | A44B 19/00 |
| WO | WO-9619126 | A1 | * | 6/1996 | A41D 20/005 |
| WO | WO-0021473 | A1 | * | 4/2000 | A61F 7/10 |
| WO | WO-02064069 | A2 | * | 8/2002 | A61F 7/02 |
| WO | WO-2008012388 | A1 | * | 1/2008 | A61F 7/10 |
| WO | 2011120752 | A1 | | 10/2011 | |
| WO | 2013004528 | A1 | | 1/2013 | |
| WO | 2016160691 | A1 | | 10/2016 | |
| WO | WO-2016183038 | A1 | * | 11/2016 | F41H 1/02 |
| WO | WO-2017116657 | A1 | * | 7/2017 | C04B 35/524 |
| WO | 2020034008 | A1 | | 2/2020 | |
| WO | WO-2022042856 | A1 | * | 3/2022 | A61F 7/02 |

OTHER PUBLICATIONS

International Search Report received in PCT/IB2024/00092, dated May 23, 2024.

International Search Report received in PCT/US19/51609 dated Jan. 30, 2020.

Nawaz et al., A Parametric Study on Mass Diffusion Coefficient of Desiccants for Dehumidification Applications: Silica Aerogels and Silica Aerogel Coatings on Metal Foams, Mar. 2015, Science and Technology for the Built Environment, vol. 21, Issue 5 (Year: 2015).

Nawaz et al., Effect of catalyst and substrate on the moisture diffusivity of silica-aerogel-coated metal foams, Jun. 2014, International Journal of Heat and Mass Transfer, vol. 73, pp. 634-644 (Year: 2014).

Nawaz, Aerogel coated metal foams for dehumidification applications, Jan. 2014, IDEALS (Illinois Digital Environment for Access to Learning and Scholarship) (Year: 2014).

Notice of Allowance received in U.S. Appl. No. 16/574,048 dated Jul. 16, 2020.

Office Action received in U.S. Appl. No. 16/574,048 dated Apr. 22, 2020.

Office Action received in U.S. Appl. No. 17/037,457 dated Jul. 22, 2022.

Office Action received in U.S. Appl. No. 18/124,283 dated May 9, 24.

Shum et al., Enhancing wicking microflows in metallic foams, Nov. 2017, Microfluidics and Nanofluidics, vol. 21 (Year: 2017).

* cited by examiner

WEARABLE COOLING SYSTEM FOR BODY COOLING AND METHOD FOR FABRICATING THE WEARABLE COOLING SYSTEM

CROSS-REFERENCE TO RELATED APPLICATIONS

This application claims the benefit of U.S. Provisional Application No. 63/450,549, filed on 7 Mar. 2023, which is incorporated in its entirety by this reference.

This application is also a Continuation-In-Part of U.S. patent application Ser. No. 18/124,283, filed on 21 Mar. 2023, which is a continuation of U.S. patent application Ser. No. 17/037,457, filed on 29 Sep. 2020, which is a continuation of U.S. patent application Ser. No. 16/574,048, filed on 17 Sep. 2019, which claims the benefit of U.S. Provisional Application No. 62/732,193, filed on 17 Sep. 2018, each of which is incorporated in its entirety by this reference.

TECHNICAL FIELD

This invention relates generally to the field of heat transfer and more specifically to a new and useful wearable heatsink and a method for fabricating the wearable heatsink in the field of heat transfer.

DESCRIPTION OF THE EMBODIMENTS

Figure 1A:
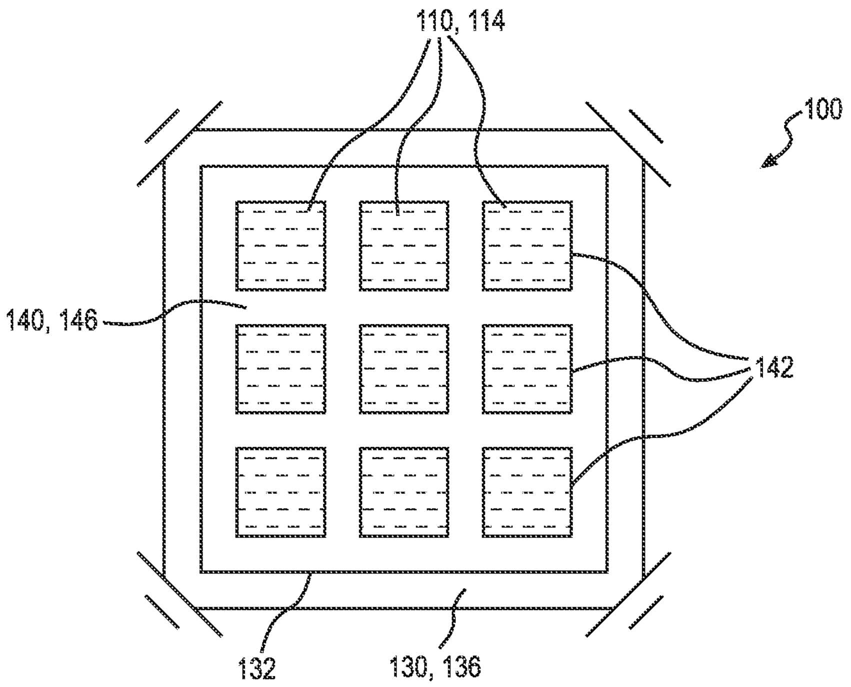
FIGS. 1A and 1B are schematic representations of a wearable cooling system.
Figure 1B:
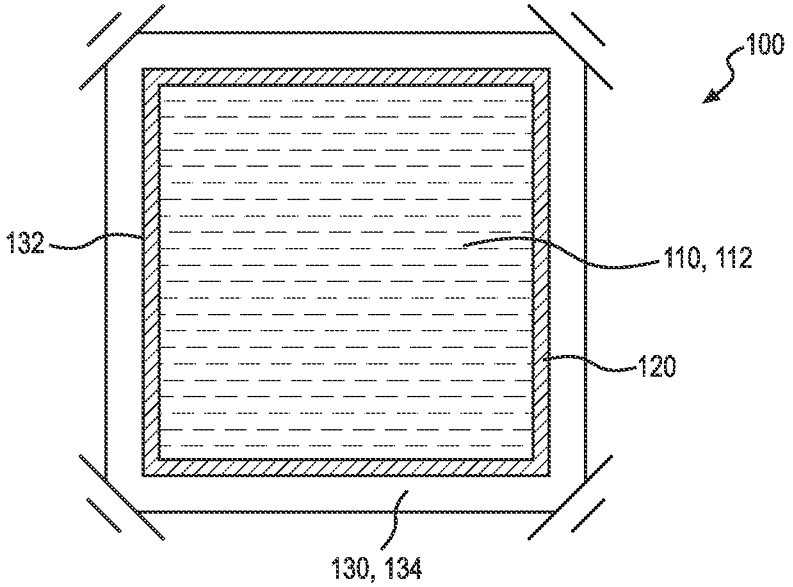

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Wearable Cooling System

As shown in FIGS. 1A, 1B, 2A, 2B, 3A, 3B, 4, 5, and 6, a wearable cooling system 100 includes a garment insert 104 and a set of cooling units 102.

The garment insert 104: is configured to be worn across a dermal surface; and includes a textile panel 130 and a set of grid structures 140. The textile panel 130 defines: an inner surface 134 configured to contact the dermal surface; an outer surface 136 opposite the inner surface 134; and a set of grid receptacles 132, each grid receptacle 132, in the set of grid receptacles 132, extending between the inner surface 134 and the outer surface 136. Each grid structure 140, in the set of grid structures 140, is arranged within and spans a grid receptacle 132, in the set of grid receptacles 132, and defines: an inner face 144 facing the inner surface 134 of the textile panel 130; an outer face 146 opposite the inner face 144 and facing the outer surface 136 of the textile panel 130; and a grid array of apertures 142 arranged in a first pattern and extending between the inner face 144 and the outer face 146 of the grid structure 140.

Each cooling unit 102, in the set of cooling units 102, is configured to transiently mate with a grid structure 140, in the set of grid structures 140, to seat within a corresponding grid receptacle 132, in the set of grid receptacles 132, and includes a heatsink structure 110 defining: a base section 112 defining an interior surface configured to contact the dermal surface; and a set of heatsink columns 114, extending from the base section 112—opposite the interior surface—and arranged in a second pattern corresponding to the first pattern, each heatsink column, in the set of heatsink columns 114, configured to seat extending through an aperture in the grid array of apertures 142. The heatsink structure 110 is configured to wick moisture from the dermal surface toward surfaces of the set of heatsink columns 114 to cool the dermal surface.

In one variation, each cooling unit 102 further includes a polymer frame 120: bonded to the heatsink structure 110 about a perimeter of the base section 112; and configured to abut surfaces of the base section 112 to surfaces of the grid receptacle 132 to flexibly retain the cooling unit 102 within the grid receptacle 132 in an assembled configuration.

In one variation, the garment insert 104 is integrated into a garment 150 configured to be worn by a user to locate the garment insert 104 across the dermal surface. In this variation, the wearable cooling system 100 further includes: a water supply 160 integrated into the garment 150 and configured to transiently store a volume of water; and a set of fluid channels 148 fluidly coupled to the water supply 160 and extending through the set of grid structures 140. In this variation, each grid structure 140, in the set of grid structures 140, defines an array of pores configured to transiently release water from fluid channels 148, in the set of fluid channels 148, extending through the grid structure 140, toward surfaces of a cooling unit 102, in the set of cooling units 102, mated with the grid structure 140 to wet the set of heatsink structures 110.

One variation of the wearable cooling system 100 includes: a garment insert 104 configured to be worn across a dermal surface; and a first cooling unit 102. The garment insert 104 includes a textile panel 130 and a first grid structure 140. The textile panel 130 defines: an inner surface 134 configured to contact the dermal surface; an outer surface 136 opposite the inner surface 134; and a first grid receptacle 132 extending between the inner surface 134 and the outer surface 136. The first grid structure 140 is arranged within and spans the first grid receptacle 132 and defines: an inner face 144 facing the inner surface 134 of the textile panel 130; an outer face 146 opposite the inner face 144 and facing the outer surface 136 of the textile panel 130; and a grid array of apertures 142 arranged in a first pattern coplanar the first grid receptacle 132.

In this variation, the first cooling unit 102 includes a first heatsink structure 110 defining: a base section 112 defining an interior surface configured to contact the dermal surface; and a set of heatsink columns 114 extending from the base section 112 and arranged in a second pattern corresponding to the first pattern, each heatsink column, in the set of heatsink columns 114, configured to seat extending through an aperture, in the grid array of apertures 142. The first heatsink structure 110 is configured to wick moisture from the dermal surface toward surfaces of the set of heatsink columns 114. The first cooling unit 102 further includes a first polymer frame 120: bonded to the first heatsink structure 110 about the base section 112; and configured to abut surfaces of the base section 112 to surfaces of the grid receptacle 132 to flexibly retain the first cooling unit 102 within the first grid receptacle 132 in an assembled configuration.

In the preceding variation, the textile panel 130 can further define a second grid receptacle 132 extending between the inner surface 134 and the outer surface 136. In this variation, the garment insert 104 can include a second grid structure 140 arranged within and spanning the second grid receptacle 132 and defining: a second inner face 144 facing the inner surface 134 of the textile panel 130 and coplanar the inner face 144; a second outer face 146 opposite the second inner face 144 and facing the outer surface 136 of the textile panel 130; and a second grid array of apertures 142 arranged in the first pattern and coplanar the second grid receptacle 132. The wearable cooling system 100 can further include a second cooling unit 102 including a second heatsink structure 110 and a second polymer frame 120. The second heatsink structure 110 defines: a second base section 112 defining a second interior surface configured to contact the dermal surface; and a second set of heatsink columns 114 extending from the second base section 112 and arranged in the second pattern corresponding to the first pattern, each heatsink column 114, in the second set of heatsink columns 114, configured to seat extending through an aperture, in the second grid array of apertures 142. The second heatsink structure 110 is configured to wick moisture from the dermal surface toward surfaces of the second set of heatsink columns. The second cooling unit 102 further includes a second polymer frame 120: rigidly coupled to the second heatsink structure 102 and arranged about the second base section 112; and configured to abut surfaces of the second base section 112 to surfaces of the second grid receptacle 132 to flexibly retain the second cooling unit 102 within the second grid receptacle 132 in the assembled configuration.

One variation of the wearable cooling system 100 includes a garment insert 104 configured to be worn across a dermal surface and a cooling unit 102. In this variation, the garment insert 104 includes a textile panel 130 defining: an inner surface 134 configured to contact the dermal surface; an outer surface 136 opposite the inner surface 134; and a grid receptacle 132 extending between the inner surface 134 and the outer surface 136. The garment insert 104 further includes a grid structure 140—arranged within and spanning the grid receptacle 132—defining: an inner face 144 facing the inner surface 134 of the textile panel 130; an outer face 146 opposite the inner face 144 and facing the outer surface 136 of the textile panel 130; and a grid array of apertures 142 arranged in a first pattern coplanar the grid receptacle 132. The wearable cooling system 100 further includes a cooling unit 102 including a heatsink structure 110 and a polymer frame 120. The heatsink structure 110 includes a substrate 116 defining: a base section 112 defining an interior surface configured to contact the dermal surface; a set of heatsink columns 114 extending from the base section 112 opposite the interior surface, defining an exterior surface, arranged in a second pattern corresponding to the first pattern, and configured to seat extending through the grid array of apertures 142 in an assembled configuration; and an open network of pores 119 extending between the interior surface and the exterior surface. The heatsink structure 110 further includes a coating 118: formed of a hydrophilic material; extending across the interior surface of the substrate and lining the open network of pores 119; defining a void network; and configured to cooperate with the substrate 116 to wick moisture from the dermal surface, through the void network lining the open network of pores 119, and to the exterior surface, to cool the dermal surface. The cooling unit 102 further includes a polymer frame 120: rigidly coupled to the heatsink structure 110 and arranged about the base section 112; and configured to abut surfaces of the base section 112 to surfaces of the grid receptacle 132 to flexibly retain the cooling unit 102 within the grid receptacle 132 in the assembled configuration.

One variation of the wearable cooling system 100 includes the garment insert 104 and the set of cooling units 102. In this variation, the garment insert 104 is integrated into a garment 150—configured to be worn across a dermal surface—and includes a textile panel 130 and a set of grid structures 140. The textile panel 130 defines: an inner surface 134 configured to contact the dermal surface; an outer surface 136 opposite the inner surface 134; and a set of grid receptacles 132, each grid receptacle 132, in the set of grid receptacles 132, extending between the inner surface 134 and the outer surface 136. Each grid structure 140, in the set of grid structures 140, is arranged within and spans a grid receptacle 132, in the set of grid receptacles 132, and defines: an inner face 144 facing the inner surface 134 of the textile panel 130; an outer face 146—opposite the inner face 144—facing the outer surface 136 of the textile panel 130; and a grid array of apertures 142—arranged in a first pattern-extending between the inner face 144 and the outer face 146 of the grid structure 140.

Each cooling unit 102, in the set of cooling units 102, includes a heatsink structure 110 and a polymer frame 120 coupled to the heatsink structure 110. The heatsink structure 110 includes a substrate 116 and a coating 118. The substrate 116 defines a base section 112—defining an interior surface configured to thermally couple to a heat source—and a set of heatsink columns 114: extending from the base section 112—opposite the interior surface—defining an exterior surface; arranged in a second pattern corresponding to the first pattern; defining an open network of pores 119 extending between the interior surface and the exterior surface; and configured to insert into the grid array of apertures 142, from the inner face 144 of the grid structure 140, to transiently seat the base section 112 against the inner face 144 of the grid structure 140 within the grid receptacle 132—and locate the interior surface of the base section 112 approximately flush the inner surface 134 of the textile panel 130—in an assembled configuration. The coating 118: is formed of a porous, hydrophilic material; extends across the interior surface of the substrate 116; lines the open network of pores 119; defines a void network configured to filter hydrophobic molecules; and is configured to cooperate with the substrate 116 to wick moisture from the dermal surface, through the void network lining the open network of pores 119, and to the exterior surface, to cool the heat source (e.g., a human body).

The polymer frame 120 is: arranged about the base section 112 of the heatsink structure 110; and configured to abut surfaces of the base section 112 to surfaces of the grid receptacle 132 to flexibly retain the cooling unit 102 within the grid receptacle 132 in the assembled configuration.

2. Method

Figure 7A:
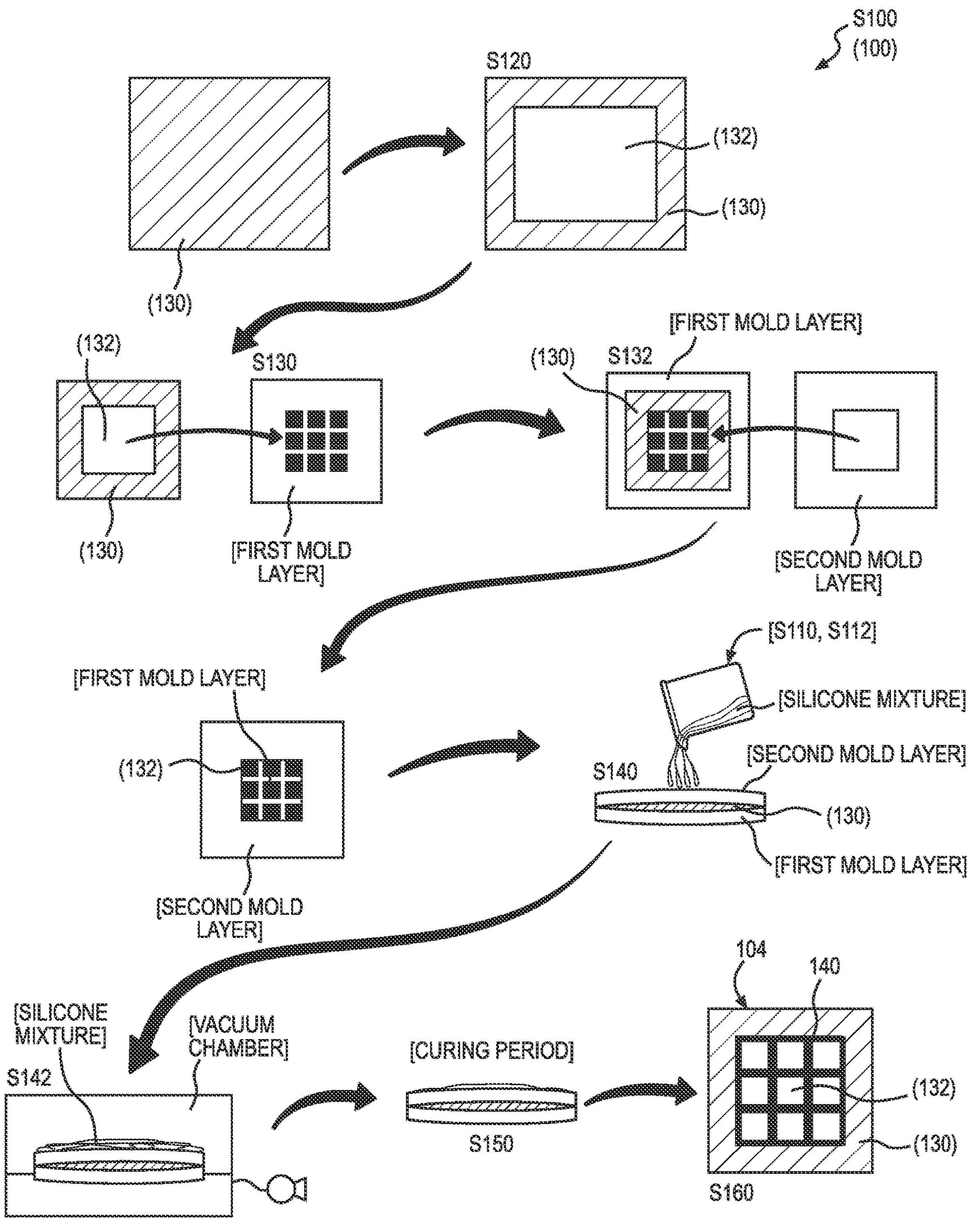
FIGS. 7A and 7B are flowchart representations of a method.
Figure 7B:
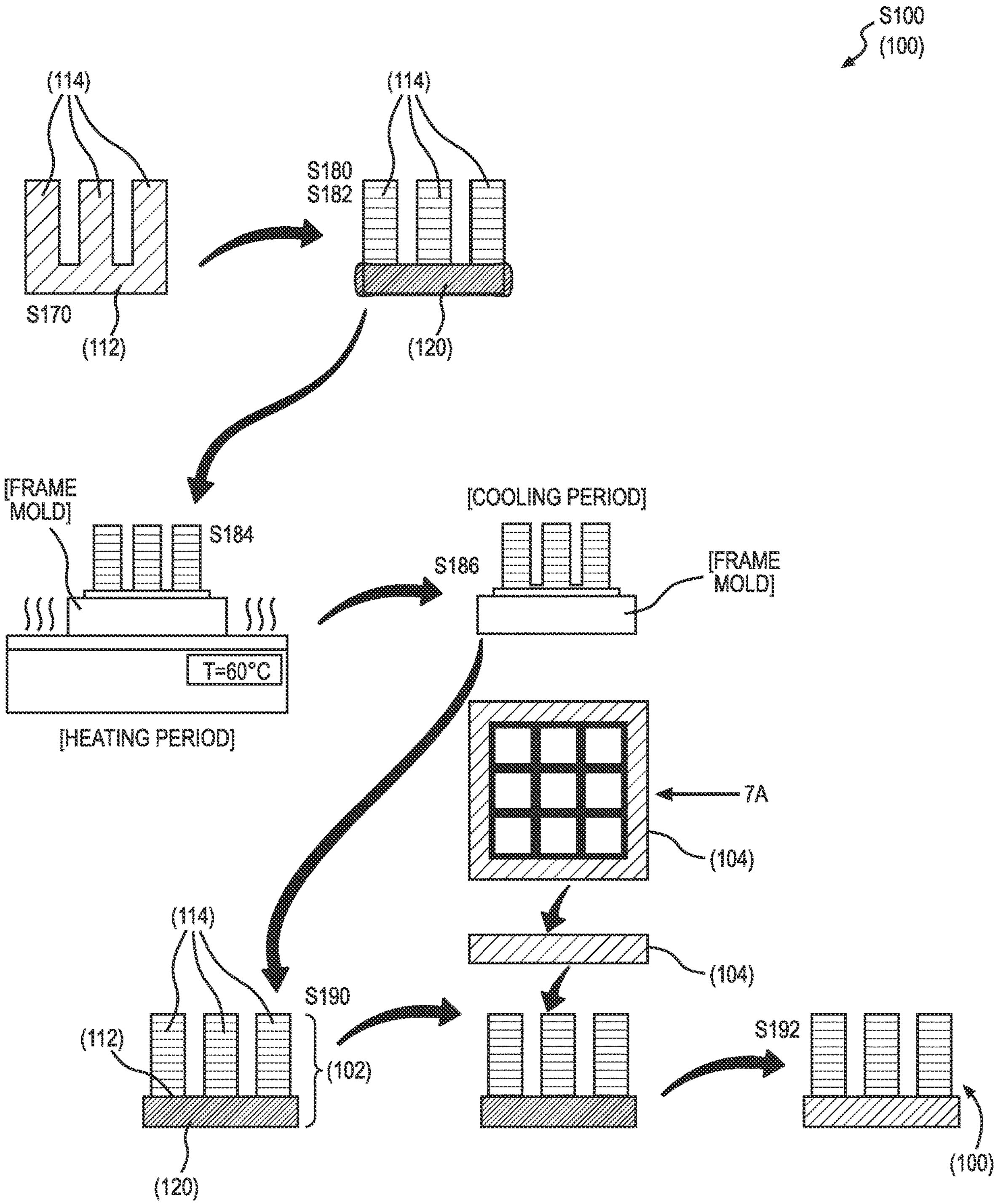

As shown in FIGS. 7A and 7B, during a first assembly period for a garment insert 104, a method S100 for fabricating a wearable cooling system 100 includes, during a preparation period: mixing a set of materials according to a mixing protocol to generate a silicone mixture in Block S110; within a vacuum chamber arranged on a vibrating surface, applying a vacuum to the silicone mixture and vibrating the silicone mixture at a target frequency to remove air bubbles from the silicone mixture in Block S112; and laser-cutting a sheet of fabric to form a textile panel 130 defining a grid receptacle 132 in Block S120. During a loading period succeeding the preparation period, the method S100 further includes: arranging the textile panel 130 over a first mold layer, of a mold housing, including a mold structure configured to seat within the grid receptacle 132 and defining a channel grid integrated into the mold structure in Block S130; arranging a second mold layer, of the mold housing—defining a column receptacle—over the textile panel 130, to locate the column receptacle over the grid receptacle 132 and seat the mold structure within the column receptacle in Block S132, the textile panel 130 interposed between the first mold layer and the second mold layer; pouring a volume of the silicone mixture over the second mold layer—and into the column receptacle—to load a subvolume of the silicone mixture into channels of the channel grid in Block S140; and locating the mold housing within the vacuum chamber for a fixed duration to remove air bubbles from the textile panel 130 and silicone mixture in Block S142. During the first assembly period, the method S100 further includes: during a curing period succeeding the loading period, retaining the textile panel 130 and the silicone material within the mold housing for a fixed duration to cure the silicone material within the channel grid to form a grid structure 140—defining a grid array of apertures 142—bonded to the textile panel 130 and arranged within the grid receptacle 132 in Block S150; and, during a finishing period succeeding the curing period, removing the textile panel 130 and the grid structure 140 from the mold housing, and removing excess silicone material from surfaces of the textile panel 130 to form the garment insert 104 in Block S160.

During a second assembly period for a cooling unit 102, the method S100 further includes: during a heatsink fabrication period, fabricating a heatsink structure 110—defining a base section 112 and a set of heatsink columns 114 extending from the base section 112—according to a heatsink fabrication protocol in Block S170; during a frame fabrication period, 3-d printing a polymer frame 120 formed of a polymer material (e.g., a polycaprolactone material) exhibiting a target flexibility in Block S180; during a loading period succeeding the heatsink fabrication period and the frame fabrication period, arranging the polymer frame 120 about a perimeter of the base section 112 and locating the base section 112 and the polymer frame 120 within a recess—defining a height approximating a height of the base section 112—of a frame mold in Block S182; during a heating period succeeding the loading period, heating the frame mold according to a heating protocol—defining a target temperature and duration—to melt the polymer frame 120 within the recess about walls of the base section 112 in Block S184; during a cooling period succeeding the heating period, cooling the frame mold to room temperature to cure the polymer frame 120 to walls of the base section 112 in Block S186; and, during a finishing period, succeeding the cooling period, removing the base section 112 and the polymer frame 120—molded to the heatsink structure 110 about the base section 112—from the recess, and removing excess polymer material—external the polymer frame 120—from surfaces of the heatsink structure 110 to form the cooling unit 102 in Block S190.

During a third assembly period succeeding the first assembly period and the second assembly period, one variation of the method S100 further includes, inserting the set of heatsink columns 114 through the grid array of apertures 142 to nest the polymer frame 120 within the grid receptacle 132 and seat the base section 112 against the grid structure 140 and within the grid receptacle 132 in Block S192.

3. Applications

Generally, Blocks of the method S100 can be executed to fabricate a wearable cooling system 100 (e.g., worn by a user) including: a garment insert 104—defining a set of grid receptacles 132—integrated into a garment 150 (e.g., a headband, an armband, a glove, a vest, a belt) configured to be worn by a user; and a set of cooling units 102 (e.g., one or more cooling units 102)—removably coupled to the set of grid receptacles 132 of the garment insert 104—configured to “cool” the user wearing the garment 150 by wicking moisture from regions of skin contacting the set of cooling units 102.

More specifically, the wearable cooling system 100 can include a garment insert 104 including a textile panel 130—defining a set of grid receptacles 132 (e.g., a cutout, an aperture, a slot)—and a set of grid structures 140, each grid structure 140 in the set of grid structures 140: rigidly coupled to the garment insert 104; arranged within and spanning a corresponding grid receptacle 132 in the set of grid receptacles 132; defining an inner face 144 and outer face 146 opposite the inner face 144; and defining a grid array of apertures 142 arranged in a grid pattern and extending between the inner face 144 and outer face 146. Further, the wearable cooling system 100 can include a set of cooling units 102, each cooling unit 102 removably coupled to a corresponding grid receptacle 132 of the textile panel 130 and including: a heatsink structure 110 defining a base section 112 and an array of heatsink columns 114 extending from the base section 112; and a polymer frame 120—rigidly coupled to the heatsink structure 110—arranged about the base section 112 and configured to abut surfaces of the base section 112 and inner walls of the cutout in an assembled configuration.

In particular, the heatsink structure 110 can be configured to wick moisture from a contact surface at one side of the heatsink structure 110 (i.e., defined by the base section 112) in contact with a human user’s skin, transport this moisture through an open network of pores 119 (e.g., via capillary action) extending through the heatsink structure 110, and raise this moisture to an evaporative surface at an opposite side of the heatsink structure 110 (i.e., defined by the array of heatsink columns 114). The polymer frame 120 can be configured to provide support to the heatsink structure 110—including the base section 112 and the array of heatsink columns 114—and retain the heatsink structure 110 within a target footprint, regardless of breaks or damage in the heatsink structure 110 over time, thereby increasing a shelf life of the cooling unit 102 and limiting decay in cooling rate over time due to damage in the heatsink structure 110. Further, by abutting surfaces of the base section 112 and the grid receptacle 132 in the assembled configuration, the polymer frame 120 can be configured to flexibly retain the base section 112 within the grid receptacle 132 and therefore reduce stress on the heatsink structure 110 in the grid receptacle 132.

In one implementation, the garment insert 104 can be configured to receive and retain a cooling unit 102 within a garment 150—containing the garment insert 104—approximately flush a dermal surface (e.g., a forehead, a forearm, a back) of a user wearing the garment 150. In particular, an inner and outer surface of the textile panel 130—rigidly coupled to the garment 150 (e.g., via sewing of the textile panel 130 to fabric forming the garment 150)—can be arranged approximately flush the inner face and outer face of the garment 150, such that the textile panel 130 and the garment 150 cooperate to form a smooth, continuous inner surface 134 in contact with the dermal surface when worn by the user. In this implementation, a user may couple a cooling unit 102 to the textile panel 130 by inserting columns of the cooling unit 102 from the inner face 144 of the textile panel 130 and through the grid array of apertures 142 within a corresponding grid receptacle 132, to seat the base section 112 on the grid structure 140 arranged within the corresponding grid receptacle 132, and thus locate an interior surface of the base section 112—configured to contact the dermal surface when worn by the user—approximately flush the inner face 144 of the textile panel 130. The textile panel 130 and the grid structure 140—arranged within the grid receptacle 132—can therefore cooperate to transiently locate and retain the cooling unit 102 within the grid receptacle 132 and maintain the interior surface of the base section 112 flush the inner face 144 of the textile panel 130 in order to maximize contact area between the interior surface and the dermal surface, thereby maximizing a cooling rate of the heatsink structure 110.

By thus decoupling the set of cooling units 102 from the garment insert 104, the wearable cooling system 100 can increase longevity or shelf life of the wearable cooling system 100 over time. For example, a user may replace an individual, damaged cooling unit 102 with a new cooling unit 102 for insertion in a particular grid receptacle 132 of the garment insert 104, rather than replace an entire garment 150 or cooling apparatus. The user may also store the set of cooling units 102 (e.g., within a protective case) separately from the garment insert 104, such as during washing of the garment insert 104 and/or during travel, to reduce wear and tear experienced by the set of cooling units 102 while enabling the user to regularly wash, wear, and/or store the garment 150 similar to the user's everyday apparel. Further, because the set of cooling units 102 can be fabricated separately from the garment insert 104, damage to these cooling units 102 during fabrication can be minimized.

In addition, the wearable cooling system 100 can enable a user to customize a configuration or arrangement of cooling units 102 installed within grid receptacles 132 of the garment insert 104—such as matched to a profile (e.g., curvature, size, shape) of a dermal surface associated with the garment insert 104—in order to maximize a contact area between the dermal surface and the set of cooling units 102 and therefore maximize the cooling rate experienced by this particular user while wearing a garment 150 containing the garment insert 104.

4. Example

Figure 2A:
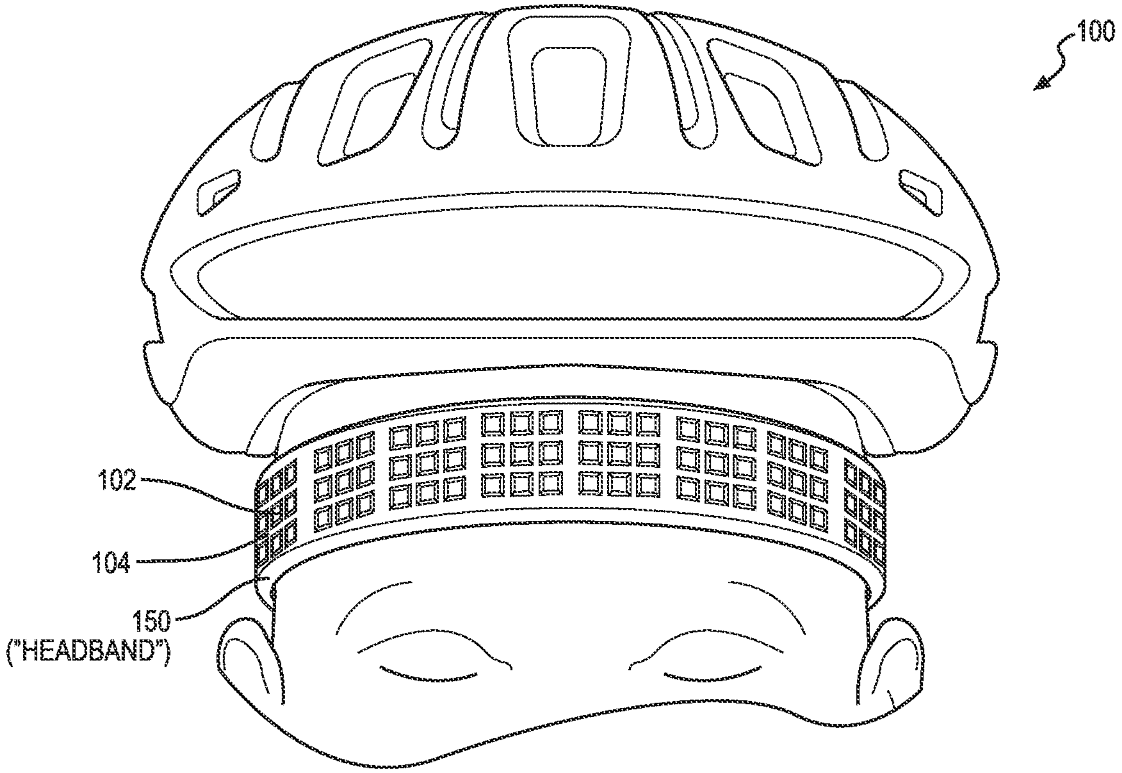
FIGS. 2A and 2B are schematic representations of variations of the wearable cooling system.
Figure 2B:
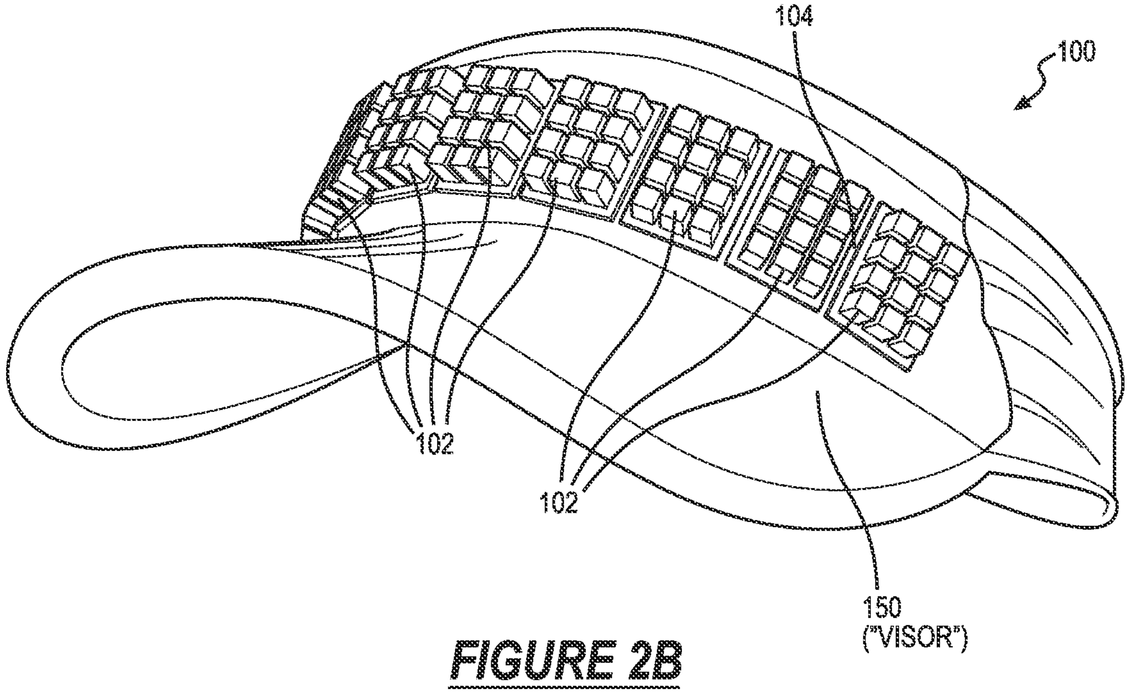
Figure 3A:
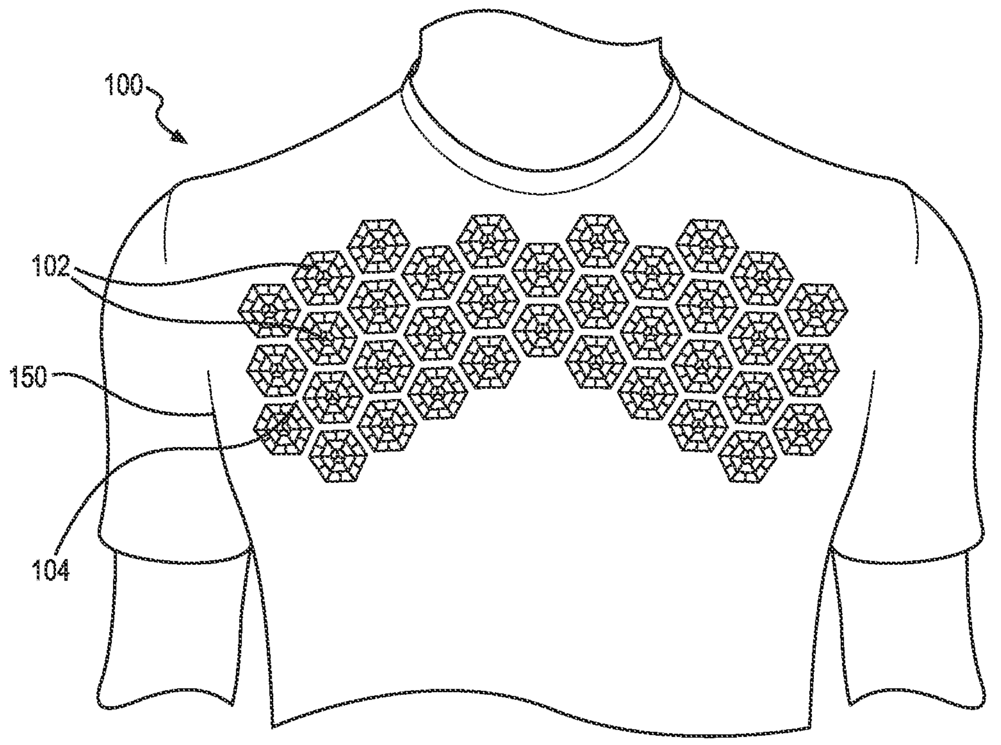
FIGS. 3A and 3B are schematic representations of variations of the wearable cooling system.
Figure 3B:
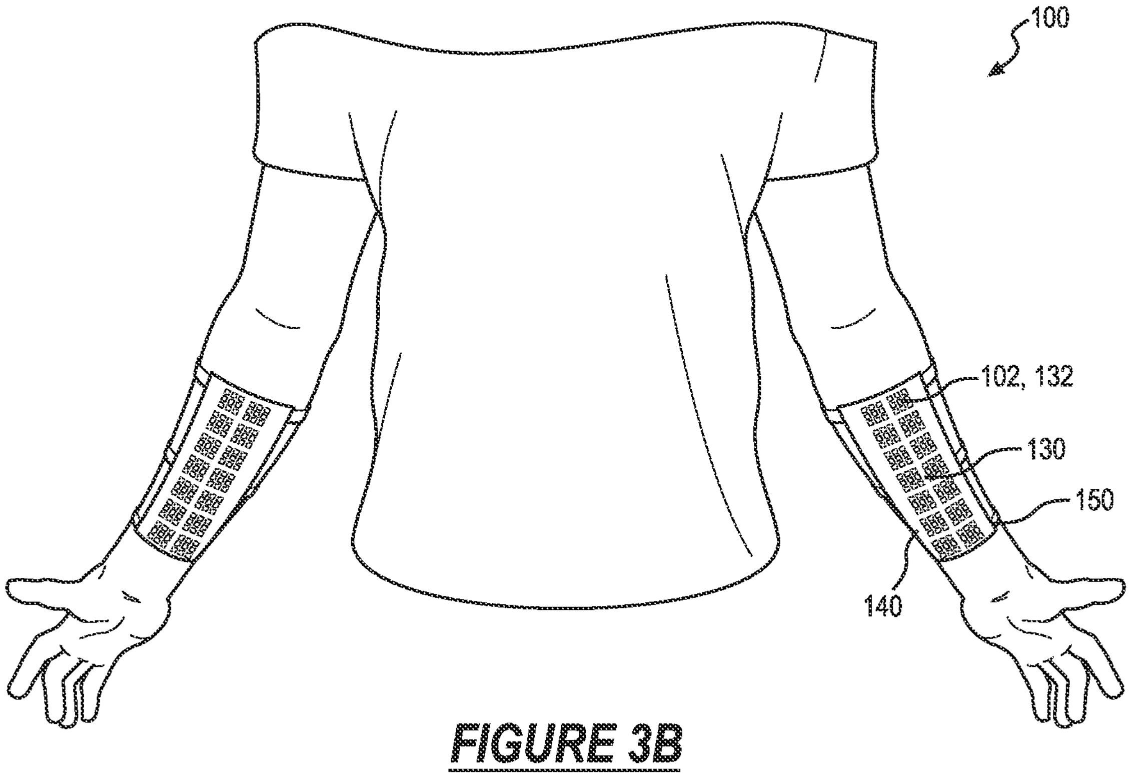
Figure 4:
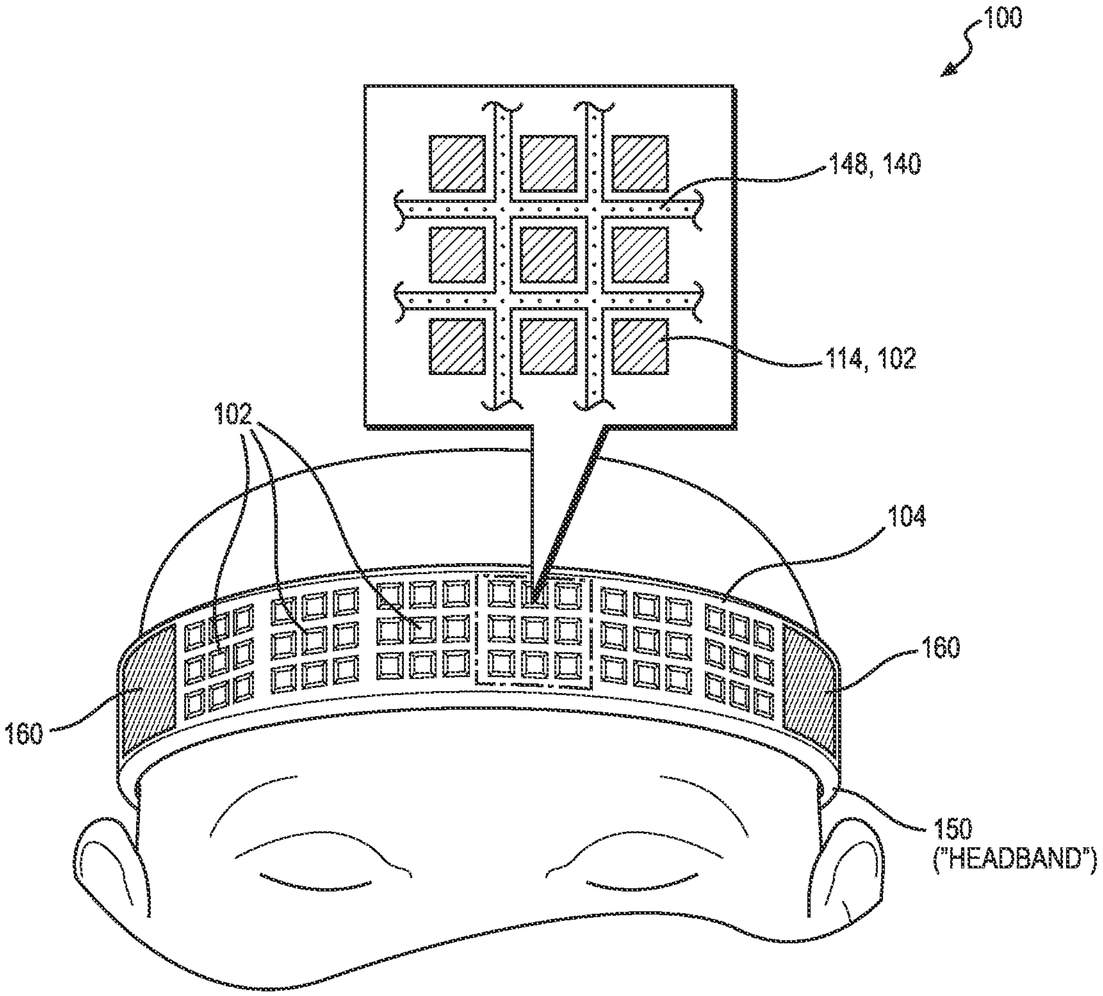
FIG. 4 is a schematic representation of one variation of the wearable cooling system.
Figure 5:
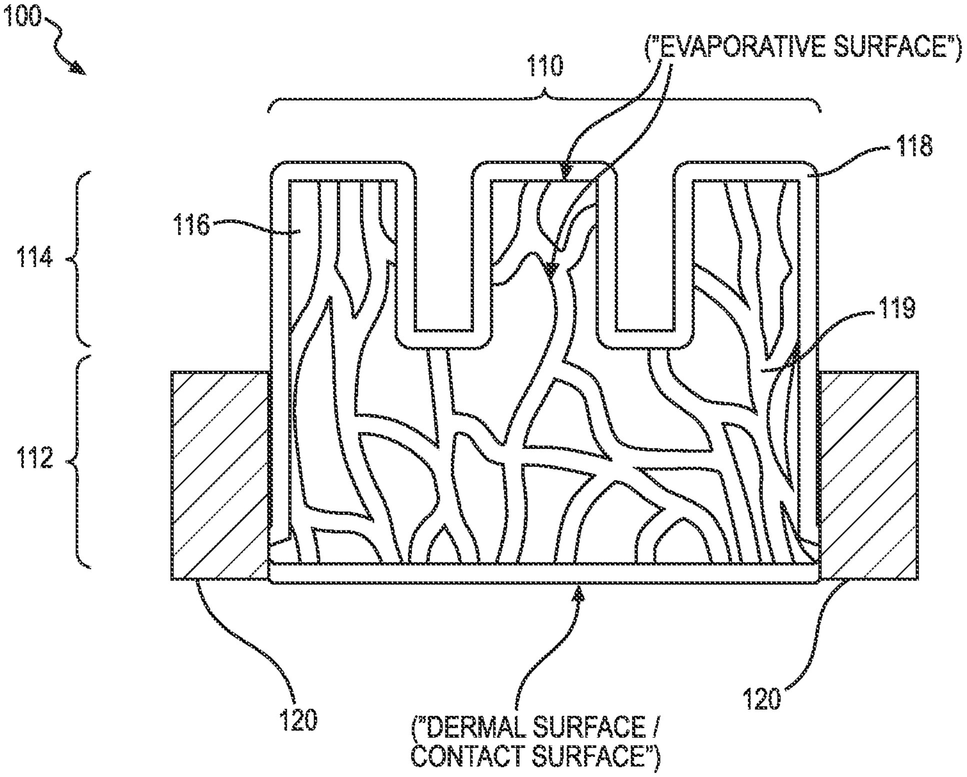
FIG. 5 is a schematic representation of one variation of the wearable cooling system.
Figure 6:
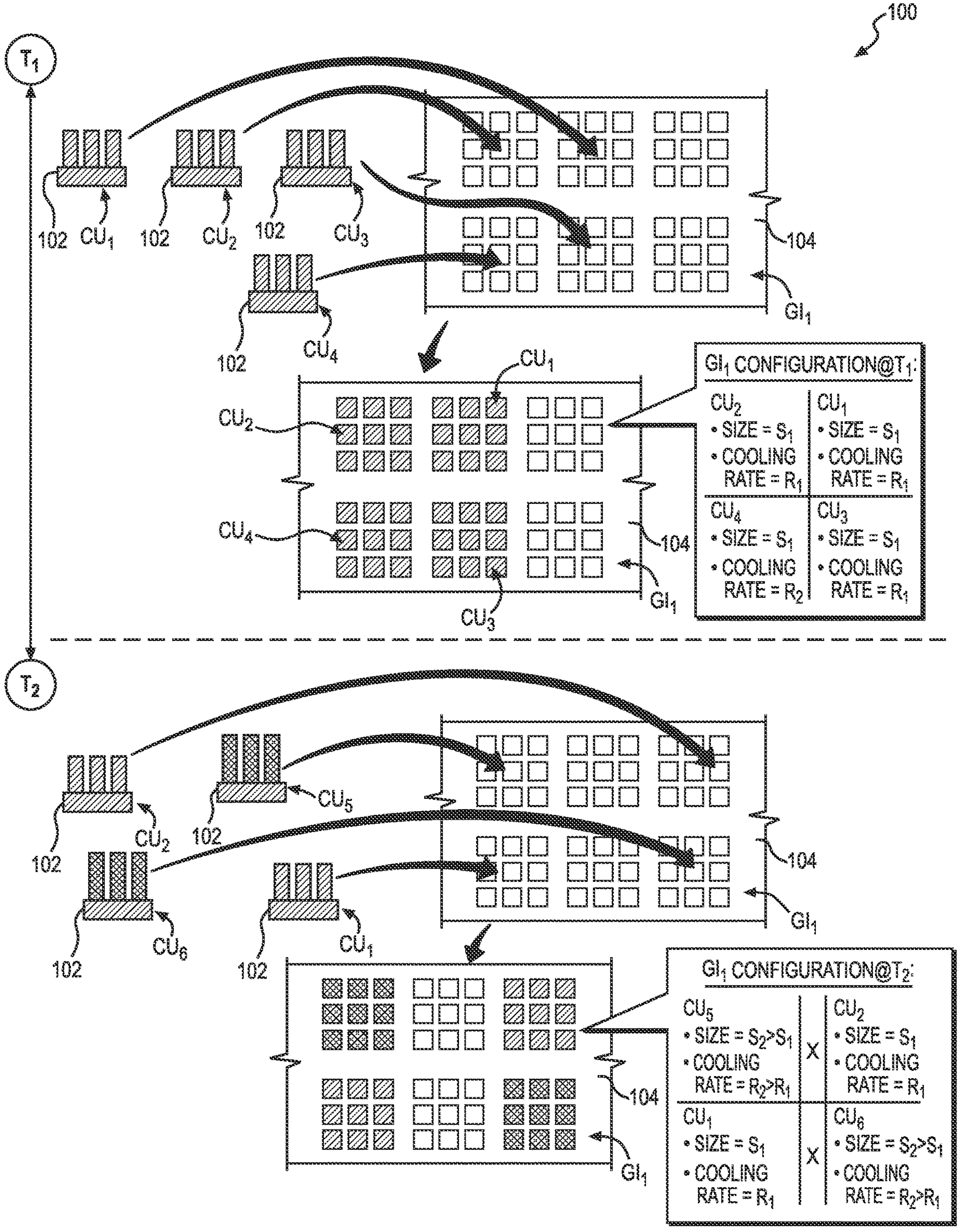
FIG. 6 is a schematic representation of one variation of the wearable cooling system.

In one example, the wearable cooling system 100 includes: a headband configured to be worn by a user about her forehead as shown in FIGS. 2A, 2B, and 4; and a set of cooling units 102 configured to transiently couple to the headband. In this example, the user may: install one or more cooling units 102 within the headband (e.g., prior to exercise); and then wear the headband—loaded with one or more cooling units 102—during exercise to wick sweat from the forehead and to cool the user as a body temperature of the user increases during exercise.

The headband can include a garment insert 104—integrated within the headband (e.g., sewn into the headband fabric)—and including: a textile panel 130 defining a set of grid receptacles 132 (e.g., laser—cut into the textile panel 130); and a set of grid structures 140, each grid structure 140 arranged within a grid receptacle 132, in the set of grid receptacle 132, and defining a grid array of apertures 142. For example, the textile panel 130 can include a set of ten, square—shaped grid receptacles 132 arranged in two symmetrical rows, and each grid structure 140 can define a grid array of nine apertures arranged in three symmetrical rows.

Each cooling unit 102 can include: a heatsink structure 110—configured to wick moisture from the forehead of the user and cool a temperature of the user when installed in the headband—defining a base section 112, configured to contact skin of the user, and an array of heatsink columns 114 extending from the base section 112; and a polymer frame 120—such as a square-shaped, polycaprolactone frame—arranged about the base section 112. For example, the heatsink structure 110 can define a set of nine heatsink columns 114 extending from the base section 112. The user may therefore transiently couple a single cooling unit 102 to a single grid structure 140 of the textile panel 130 by inserting the set of heatsink columns 114 through the grid array of apertures 142 to nest the polymer frame 120—abutting surfaces of the heatsink structure 110 and the grid receptacle 132—within the grid receptacle 132 and thus seat the base section 112 within the grid receptacle 132. In particular, the base section 112 can seat within the grid receptacle 132 such that an interior face of the base section 112 seats approximately flush an inner surface 134 of the headband—configured to contact skin of the user when worn by the user—and an outer face 146 of the base section 112 mates with the grid structure 140.

Additionally and/or alternatively, the wearable cooling system 100 can include: a wristband configured to be worn by a user about her forearm; a visor configured to be worn by a user about her forehead or head; a vest configured to be worn by a user about her back and/or chest; etc.

For example, the garment insert 104 can be integrated into a headband configured to be worn across a forehead of a human user. In this example, the inner surface 134 of the textile panel 130 can be configured to contact the forehead of the user and each heatsink structure 110—of a particular cooling unit 102—can be configured to wick moisture from the forehead toward surfaces of the set of heatsink columns 114 of the heatsink structure 110 to cool the forehead (i.e., the dermal surface) and therefore the human user. In another example, the garment insert 104 can be integrated into an armband configured to be worn across a forearm of a human user. In this example, the inner surface 134 of the textile panel 130 can be configured to contact the forearm of the user and each heatsink structure 110—of a particular cooling unit 102—can be configured to wick moisture from the forearm toward surfaces of the set of heatsink columns 114 of the heatsink structure 110 to cool the forearm (i.e., the dermal surface) and therefore the human user.

In each of these examples, the user may rapidly install, remove, and/or transfer couple cooling units 102, from the set of cooling units 102, to one or more garments 150 (e.g., headband, wristband, visor, vest) selected by the user, such as for wearing during a particular exercise.

5. Heatsink Structure

Generally, the cooling unit 102 can include a heatsink structure 110 including: a substrate 116 defining an open network of pores 119 (or "open-celled pores" or "channels"); and a coating 118 of a porous hydrophilic material that lines internal and external surfaces of the substrate 116—including walls of the open network of pores 119 in the substrate 116. As described in U.S. patent application Ser. No. 16/574,048, filed on 17 Sep. 2019—which is incorporated in its entirety by this reference—the coating 118 can form a robust shell around the substrate 116 and can function to wick moisture from a contact surface at one side of the heatsink structure 110 in contact with a human user's skin, transport this moisture through the open network of pores 119 in the substrate 116 (e.g., via capillary action), and raise this moisture to an evaporative surface defined by surfaces of the coating 118 at an opposite side of the heatsink structure 110 and within the internal network of pores 119. The evaporative surface can span a set of fins (or "heatsink columns 114") across the heatsink structure 110 and may be cooled via evaporative cooling as moisture—drawn from the contact surface through the void network 121 of the coating 118 lining the open network of pores 119 in the substrate 116—evaporates. Accordingly, the substrate 116 draws heat from the user's skin at the contact surface and conducts this heat to the evaporative surface, which releases this heat to the environment (e.g., via convection and radiation), thereby cooling the user. In particular, the method S100 can be executed to fabricate a heatsink structure 110 that includes a conductive, porous substrate 116 lined with a hydrophilic, porous coating 118 such that the heatsink structure 110: defines a dense open network of pores 119 with sufficient pore size such that air may flow freely through pores and the available surface area for application of the coating 118 is increased. The coating 118 defines a void network 121 (or "porous microstructure") with minimal void (or "pore") size exhibiting low resistance to transport of moisture (e.g., high permeability to water) between the contact surface (adjacent the interior surface of the substrate 116) and surfaces of the coating 118 within the open network of pores 119 and the evaporative surface (adjacent the external surface of the substrate 116), and exhibits high resistance to transport of other organic molecules (e.g., oils) through the void network 121. For example, the dense open network of pores 119 defined by the heatsink structure 110 can exhibit pore sizes large enough to be lined by the coating 118 and for effective flow of air through pores in the open network of pores 119, and the coating 118 can be processed such that at room temperature conditions, the void network 121 of the coating 118 is hydrated (e.g., the pores are filled with water molecules) and therefore hydrophilic (e.g., attracted to water molecules) and contaminant resistant due to the size of pores in this void network 121 (e.g., larger hydrophobic molecules cannot displace the smaller water molecules present in these hydrated pores). The heatsink structure 110 may therefore be hydrophilic and exhibit contaminant resistant properties (e.g., contaminant resistant) properties due to the hydrated void network 121 of the coating 118 lining the open network of pores 119.

The resulting heatsink structure 110 can thus define: a porous, thermally-conductive structure (i.e., the substrate 116) with a network of interconnected pores encased in a rigid, hydrophilic shell (i.e., the coating 118) that exhibits greater affinity to polar substances (e.g., water) than to non-polar substance (e.g., oil). The coating 118 thus forms hydrophilic surfaces that are resistant to hydrophobic contaminants, such as volatile organic compounds (VOCs) and oils; by spanning interior and exterior surfaces of the substrate 116, the coating 118 thus increases hydrophilicity and increases resistance of the heatsink structure 110. More specifically, this greater affinity of the coating 118 to polar substances enables water to wet surfaces of the heatsink structure 110 when oils and other contaminants are present at these surfaces, such as at the contact surface when the contact surface is placed in contact with a user's forehead, forearm, or chest. Additionally, because the coating 118 exhibits a relatively high affinity to polar substances, the heatsink may be quickly cleaned of oils and other contaminants by rinsing with water and/or surfactants (e.g., soap). Therefore, a heatsink structure 110 defining a durable, contaminant resistant wicking structure (e.g., heatsink) exhibiting hydrophilicity, contaminant resistance, and high thermal conductivity can be fabricated according to Blocks of the method S100.

5.1 Substrate

Generally, the heatsink structure 110 includes a substrate 116 defining: an interior surface configured to thermally couple to a heat source; an exterior surface; and an open network of pores 119 extending between the interior surface and the exterior surface. More specifically, the substrate 116 exhibits a particular geometry including a fin side defining the exterior surface, and a body side defining the interior surface. The substrate 116 is lined with a porous, hydrophilic coating 118 to form the heatsink structure 110. The substrate 116 further defines: a base defining the interior surface, the base exhibiting a first surface area; and a set of heatsink columns 114 extending from the base opposite the interior surface, the set of heatsink columns 114 exhibiting a second surface area greater than the first surface area and defining the exterior surface.

The substrate 116 exhibits a high thermal conductivity and is configured to dissipate heat from a heat source (e.g., transfer heat from a heat source to the exterior surface of the substrate 116). The interior surface of the substrate 116 is configured to thermally couple to the heat source to enable heat dissipation from the smaller surface area of the interior surface to the greater surface area of the evaporative surface, defined by the surface area of the exterior surface (e.g., the fins of the substrate 116) and the surface area of the walls of the network of pores 119. A coating 118 deposited over surfaces of the substrate 116 to increase hydrophilicity of the heatsink structure 110 may exhibit decreased thermal conductivity of the heatsink structure 110. Therefore, a material exhibiting high thermal conductivity can be machined or molded to form the substrate 116 in order to maximize the thermal conductivity of the heatsink structure 110 after addition of the coating 118 to surfaces of the substrate 116.

The thermally conductive substrate 116 can exhibit a porous structure and define an open network of pores 119, through which moisture can flow from the interior surface of the substrate 116 to the exterior surface of the substrate 116. These pores exhibit sufficiently small volumes such that moisture can be absorbed through the pores via capillary action, while larger molecules contained in oils and other contaminants cannot travel through the pores.

For example, the substrate 116 can define an open network of pores 119 including pores exhibiting pore diameters between 275-microns and 325-microns such that sufficient capillary pressure is generated for water to flow through the open network of pores 119. In a similar example, the substrate 116 defines the open network of pores 119 exhibiting a pore size less than 400 microns, and the coating 118 defines a thickness between 50 microns and 200 microns to yield an effective pore size less than 100 microns on walls of the open network of pores 119 in the substrate 116. The substrate 116 and the coating 118—in the completed heatsink structure 110—can therefore cooperate to wick moisture (e.g., sweat) from the interior surface to the exterior surface via the open network of pores 119 (e.g., via capillary action) when the heatsink structure 110 is in contact with a user's skin.

Additionally, the substrate 116 may exhibit higher mechanical durability with decreased pore size. Therefore, the substrate 116 can include more intricate base and fin features which may increase a rate of heat dissipation from a heat source to the heatsink structure 110.

The substrate 116 can be formed from a thermally conductive foam such as: aluminum foam, copper foam, or graphite foam. These foams exhibit porous structures and therefore exhibit relatively high specific surface areas (e.g., surface area per volume). Thermally conductive foams also exhibit relatively lower density than traditional metals included in heat sinks, due to their porous structure.

In one implementation, the substrate 116 is machined from a thermally conductive graphite material defining an open network of pores 119. The conductive graphite material can be a graphite foam (e.g., Graphite Foam produced by C-FOAM Corporation of Western Australia). For example, the substrate 116 can be machined from a block of graphite foam, the graphite foam exhibiting high thermal conductivity and low density. Generally, graphite foams can be made by: selecting a mold configured to shape the graphite foam and applying a mold release agent to walls of the mold; introducing a quantity of pitch to the mold; purging the mold of air via applying a vacuum or introducing an inert fluid; heating the pitch in the mold to a sufficient temperature such that the pitch coalesces into a liquid (e.g., between 50° Celsius and 100° Celsius higher than the softening point of the pitch); releasing the vacuum and applying an inert fluid at a static pressure (e.g., approximately 1000-psi); further heating the pitch to a high temperature such that gases evolve and foam the pitch; and further heating the pitch to a higher temperature to coke the pitch before cooling the pitch to room temperature, while gradually releasing the applied static pressure. The resulting porous graphite foam may be machined to form the substrate 116.

In one implementation, the substrate 116 is molded from a metallic material, such as aluminum or copper. In this implementation, the substrate 116 can be molded to fit a particular size and geometry.

The substrate 116 can be machined to a particular shape and size. In one variation, the substrate 116 exhibits a quadrangular prism shape and defines straight, narrow channels on an upper section of the substrate 116 to form a set of heatsink columns 114. The substrate 116 can include the set of heatsink columns 114 to increase a surface area of the exterior surface, and therefore increase the rate of heat dissipation from a heat source. The interior surface of the substrate 116 can be straight or curved to match a shape of regions of the human body. For example, the interior surface of a substrate 116 may be curved to fit the curvature of a forehead of user. Alternatively, the interior surface of the substrate 116 may be flat (e.g., straight edges) and include gaps between heatsinks to enable bending or greater flexibility of the wearable cooling system 100 about regions of the body such that the wearable cooling system 100 can be worn by different users and conform to each user accordingly.

5.2 Coating

The heatsink structure 110 includes a coating 118 lining each surface of the substrate 116 and the walls of pores in the networks of pores within the substrate 116. The coating 118 forms: an interior shell extending across the interior surface of the substrate 116 and defining a contact surface configured to contact skin of a user, the contact surface defining a first area; and an exterior shell extending across the exterior surface of the substrate 116 and defining an evaporative surface of a second area greater than the first area.

Generally, the coating 118 functions as a hydrophilic shell cooperating with the substrate 116 to enable moisture wicking from skin of a user across a contact surface of the coating 118, through the open network of pores 119 of the substrate 116, and across an evaporative surface of the coating 118, and to provide durability to the heatsink structure 110. The coating 118 can define a cementitious mixture exhibiting high water concentration such that the water molecules in the coating 118 attract water molecules in moisture passing through the open network of pores 119 within the substrate 116, therefore exhibiting hydrophilic properties. The coating 118 also functions as a contaminant resistant layer to prevent contaminants such as oils from clogging the open network of pores 119.

The coating 118 can define a thin shell of approximately uniform thickness that: extends across the exterior surface of the substrate 116; extends across the interior surface of the substrate 116; and lines the walls of the open network of pores 119 within the substrate 116. In particular, the coating 118 can be of at least a minimum thickness across the surfaces of the substrate 116 in order to increase durability of the heatsink structure 110 and increase resistance of the heatsink structure 110 to oils and other contaminants. The coating 118 can be less than a maximum thickness in order to maintain the open network of pores 119 within the substrate 116 and preserve the heat exchanger properties of the structure provided by the substrate 116, as the coating 118 is less thermally conductive than the substrate 116. For example, the heatsink structure 110 can include a substrate 116 machined from a graphite foam material and exhibiting a first impact resistance. The heatsink structure 110 can also include a coating 118: defining a cementitious matrix and exhibiting a second impact resistance greater than the first impact resistance, such that coating 118 increases a durability of the heatsink structure 110; and exhibiting a thickness between 75-microns and 125-microns.

In one implementation, the coating 118 is a cementitious mixture of distilled water and cement (e.g., Portland white cement). To prepare the coating 118 for application onto the substrate 116, a volume of water is mixed with a volume of cement (and an aggregate) at a water-cement ratio that—when cured—yields a heterogeneous microstructure including a pore structure, cement, and interfacial transition zone that are permeable to water. More specifically, the coating 118 can harden as a result of a chemical reaction between water and cement in this cementitious mixture. At a low water-cement ratio (e.g., less than 0.4), this reaction in the coating 118 is fully hydrated but may exhibit a water permeability insufficient to wet and fully coat the substrate 116. Further, at low and moderate water-cement ratios (e.g., 0.35 to 0.65), the coating 118 may exhibit minimal porosity, exhibit a network of narrow pores, and thus exhibit relatively low permeability to water when cured. Therefore, the coating 118 can be prepared with a relatively high water-cement ratio (e.g., greater than 0.7; or within the range of 0.78 to 0.82) such that the reaction between water and cement in the cementitious mixture yields excess water as the coating 118, thereby resulting in the coating 118 exhibiting a highly porous microstructure that is permeable to water, therefore resulting in greater moisture flux through the resulting heatsink structure 110.

For example, the coating 118 can define a cementitious mixture of water and calcium silicate cement mixed at a water-cement ratio between 0.8 and 1.0 to achieve high porosity and increase hydrophilic tendencies of the coating 118.

Furthermore, the coating 118 defines a void network 121 configured to filter hydrophobic molecules and increase the hydrophilicity of the coating 118 and thereby the heatsink structure 110. The coating 118 can define the void network 121 including: micropores that wick water through the coating 118, and that exhibit a first size smaller than pores in the network of pores 119; and nanopores that are hydrated at standard conditions (e.g.,) to increase the hydrophilicity of the coating 118, and that exhibit a second size smaller than the first size such that larger hydrophobic molecules cannot displace water in the hydrated nanopores. The coating 118—defining this void network—lines the network of pores 119 of the substrate 116 to wick moisture through the coating 118 while larger pores in the network of pores 119 provide an increased heat exchange surface and enable airflow through the heatsink structure 110.

5.3 Heatsink Structure: Target Cooling Rate

In one variation, the heatsink structure 110 can be configured to exhibit a target cooling rate when worn by a user—within the garment insert 104—to cool a region of the user's body.

In one implementation, the heatsink structure 110 can be configured to include a set of heatsink columns 114 of a target height corresponding to a target cooling rate defined for the heatsink structure 110. For example, a first heatsink structure 110—defining a first target cooling rate—can include a first set of heatsink columns 114 of a first height proportional the first target cooling rate. A second heatsink structure 110—defining a second target cooling rate exceeding the first target cooling rate—can include a second set of heatsink columns 114 of a second height exceeding the first height and proportional the second target cooling rate. In particular, in this example, by increasing a height of the second set of heatsink columns 114, the second heatsink structure 110 can exhibit a larger evaporative surface than the first heatsink structure 110 and therefore release heat—at the evaporative surface—at an increased rate. By thus modifying a height of the set of heatsink columns 114 and therefore modifying size of the evaporative surface, the heatsink structure 110 can be configured to exhibit a particular cooling rate proportional this height of the set of heatsink columns 114.

Additionally and/or alternatively, in another implementation, the heatsink structure 110 can be configured to include a volume of a coating 118—applied to surfaces of the substrate 116—corresponding to the target cooling rate defined for the heatsink structure 110. For example, a first heatsink structure 110 defining a first target cooling rate can include a first volume of the coating 118—applied to surfaces of a first substrate 116 of the first heatsink structure 110—proportional the first target cooling rate. A second heatsink structure 110 defining a second target cooling rate, exceeding the first target cooling rate, can include a second volume of the coating 118—applied to surfaces of a second substrate 116 of the second heatsink structure 110—exceeding the first volume and proportional the second target cooling rate. By thus modifying the volume of the coating 118 applied to the substrate 116, the heatsink structure 110 can be configured to exhibit a particular cooling rate proportional this volume of the coating 118.

6. Garment Insert

The wearable cooling system 100 can include a garment insert 104—integrated into and/or configured for integration within a garment 150—configured to transiently receive a cooling unit 102 to integrate the cooling unit 102 within the garment 150. Generally, the garment insert 104 can include: a textile panel 130 (e.g., a sheet of fabric) defining a grid receptacle 132; and a grid structure 140 integrated within the grid receptacle 132 and configured to transiently mate with features of the cooling unit 102 to locate the cooling unit 102 within the grid receptacle 132. In particular, the grid structure 140 can be: arranged within the grid receptacle 132—rigidly coupled to walls of the grid receptacle 132 about a perimeter of the grid structure 140—such that the textile panel 130 forms a substantially rigid frame or perimeter about the grid structure 140; and configured to transiently receive and retain a cooling unit 102 within the grid receptacle 132.

For example, the garment insert 104 can be configured to receive and retain a cooling unit 102 within a garment 150—containing the garment insert 104—and approximately flush a dermal surface (e.g., a forehead, a forearm) of a user wearing the garment 150. In particular, in this example, the garment insert 104 can include a textile panel 130: rigidly coupled to the garment 150 (e.g., via sewing of the textile panel 130 to fabric forming the garment 150); defining an inner and outer face 146 arranged approximately flush inner and outer face 146*s* of the garment 150, such that the textile panel 130 and the garment 150 cooperate to form a smooth, cohesive inner face 144—configured to contact a dermal surface—and a smooth, cohesive outer surface 136; and defining a grid receptacle 132 extending between the inner and outer face 146. The textile panel 130 can further include a grid structure 140—rigidly coupled to and spanning the grid receptacle 132—defining a grid array of apertures 142. In this example, a user may couple a cooling unit 102 to the textile panel 130 by inserting columns of the cooling unit 102 from the inner face 144 of the textile panel 130 and through the grid array of apertures 142 within the grid receptacle 132, to seat a base surface of the cooling unit 102—configured to contact the dermal surface—approximately flush the inner face 144 of the textile panel 130.

In one implementation, the garment insert 104 can include a textile panel 130—defining a set of grid receptacles 132—and a set of grid structures 140, each grid structure 140, in the set of grid structures 140: arranged within a particular grid receptacle 132 in the set of grid receptacles 132; and configured to transiently receive and retain a cooling unit 102 within the grid receptacle 132. For example, the garment insert 104 can include: a textile panel 130 defining a first grid receptacle 132 and a second grid receptacle 132; a first grid structure 140 arranged within the first grid receptacle 132 and configured to transiently receive and retain a first cooling unit 102 within the first grid receptacle 132; and a second grid structure 140 arranged within the second grid receptacle 132 and configured to transiently receive and retain a second cooling unit 102 within the second grid receptacle 132. The garment insert 104 can similarly include a third grid structure 140 arranged within a third grid receptacle 132, a fourth grid structure 140 arranged within a fourth grid receptacle 132, etc.

Therefore, the garment insert 104 can be configured to include an array of grid receptacles 132—each including a grid structure 140 rigidly arranged within the grid receptacle 132—configured to locate a set of cooling units 102 in a substantially planar arrangement, such that the set of cooling units 102 seat approximately flush across a dermal surface (e.g., a forehead) of a user when the user wears a garment 150 including the garment insert 104 that locates the garment insert 104 across this dermal surface.

In one variation, the garment insert 104 can be configured to affix directly to a dermal surface (e.g., a forehead, a forearm) of a user, such as without integration of the garment insert 104 into a garment 150. For example, the garment insert 104 can be configured to include an adhesive layer—arranged across an inner surface 134 of the textile panel 130 (e.g., an adhesive tape or film, a cloth layer)—configured to affix the inner surface 134 of the textile panel 130 to the dermal surface.

6.1 Textile Panel

Generally, the garment insert 104 includes a textile panel 130—integrated into a garment 150 configured to be worn by a user—defining a set of grid receptacles 132 configured to transiently receive and retain a set of cooling units 102. In particular, the textile panel 130 can define: an inner surface 134; an outer surface 136 opposite the inner surface 134; and a set of grid receptacles 132—arranged in a particular pattern—extending between the inner surface 134 and the outer surface 136. For example, the garment insert 104 can include one or more layers of fabric (e.g., arranged in a stack) defining a set of grid receptacles 132 extending through each layer of fabric. In this implementation, each grid receptacle 132, in the set of grid receptacles 132, can include a grid structure 140 arranged within and spanning the grid receptacle 132.

Further, in one implementation, the textile panel 130 can be configured to exhibit a target height, such that each grid receptacle 132, in the set of grid receptacles 132, exhibits the target height. In particular, each grid receptacle 132 can be configured to exhibit a target height exceeding a height of a grid structure 140 arranged within the grid receptacle 132, in order to enable seating of the base section 112 of the cooling unit 102 within the grid receptacle 132 and on the grid structure 140—such as with minimal extension of the base section 112 beyond the inner surface 134 of the textile panel 130—in the assembled configuration. In particular, the grid receptacle 132 can be configured to seat the base section 112 of the cooling unit 102 on the inner face 144 of the grid structure 140 in the assembled configuration; and locate the base surface of the base section 112—configured to contact the dermal surface—approximately flush the inner surface 134 of the textile panel 130 in the assembled configuration.

6.2 Grid Structure

Generally, the garment insert 104 can include a grid structure 140 spanning a grid receptacle 132 of the textile panel 130.

In one implementation, the grid structure 140 defines: an inner face 144; an outer face 146 opposite the inner face 144; and a grid array of apertures 142—extending between the inner and outer face 146*s*—arranged in a grid pattern. In this implementation, the grid array of apertures 142 can be configured to transiently receive heatsink columns 114 of the cooling unit 102 to seat the base structure of the cooling unit 102 on an inner face 144 of the grid structure 140 and locate the cooling unit 102 in the assembled configuration, heatsink columns 114 of the cooling unit 102 extending from the base structure and through the grid array of apertures 142 in the assembled configuration.

In one implementation, the grid structure 140 can be formed of a silicone material configured to enable contouring of the garment insert 104 about a dermal surface when worn by a user. In particular, in this implementation, the garment insert 104 can include a silicone grid structure 140 arranged within the grid receptacle 132. This silicone grid structure 140 can be configured to exhibit a target flexibility to enable bending or contouring of the garment insert 104 about the dermal surface (e.g., a user's forehead, a user's forearm). For example, the silicone grid structure 140 can be configured to bend about a user's forehead without breaking or exhibiting structural damage. Further, by enabling contouring of the garment insert 104 about the dermal surface, the silicone grid structure 140 can be configured to maximize a thermal contact area between surfaces of the cooling unit 102 and the dermal surface and therefore maximize a rate of cooling of the user wearing the garment insert 104 across the dermal surface.

Additionally, this silicone grid structure 140 can be configured to securely locate the cooling unit 102 within the grid receptacle 132 of the garment insert 104 by: receiving columns of the cooling unit 102 within the grid array of apertures 142; and seating the base section 112 of the cooling unit 102 against the inner face 144 of the silicone grid structure 140. In particular, the inner face 144 of this silicone grid structure 140 can flexibly receive an upper surface of the base section 112—heatsink columns 114 extending from this upper surface of the base section 112—and contour about the upper surface, thereby increasing contact area between the upper surface of the base section 112 and the inner face 144 of the silicone grid structure 140 in the assembled configuration. Further, in the assembled configuration, inner surface of the silicone grid structure 140—extending between the inner and outer face 146 and forming walls of the grid array of apertures 142—can contour about surfaces of the heatsink columns 114 seated within the grid array of apertures 142, thereby further increasing contact area between the silicone grid structure 140 and the cooling unit 102. In particular, in one implementation, the grid structure 140 can be configured to exhibit at least a threshold height—coaxial the grid receptacle 132—in order to achieve at least a threshold contact area between the grid structure 140 and the array of heatsink columns 114. Therefore, by increasing this contact area, the silicone grid structure 140 can be configured to increase an amount of friction between surfaces of the silicone grid structure 140 and surfaces of the base structure and heatsink columns 114 of the cooling unit 102, and therefore reduce risk of accidental dislocation of the cooling unit 102 from the garment insert 104.

6.2.1 Grid Array of Apertures

Generally, the grid structure 140 defines a grid array of apertures 142 configured to transiently receive and retain heatsink columns 114 of the cooling unit 102 within the grid receptacle 132.

In one implementation, the grid array of apertures 142 can be arranged in a particular grid pattern corresponding to a column pattern of the cooling unit 102. Further, in this implementation, each aperture, in the grid array of apertures 142, can be configured to exhibit a particular geometry—such as a length, a width, and/or a shape—corresponding to a geometry of a corresponding heatsink column 114 of the cooling unit 102. In one example, the garment insert 104 can include a grid structure 140 defining a grid array of nine apertures arranged in a substantially square pattern (e.g., a 3 by 3 grid array of apertures 142). Each aperture, in the array of nine apertures, can define a first cross-section of a first shape (e.g., a square cross-section, a rectangular cross-section). In this example, the cooling unit 102 can define a set of nine heatsink columns 114 extending from the base section 112 and arranged in the substantially square pattern. Each heatsink column, in the set of nine heatsink columns 114, can define a second cross-section of the first shape and smaller than the first cross-section—such as within a threshold deviation of the first cross-section—such that the set of nine heatsink columns 114 insert through and nest within the set of nine apertures, in the grid array of apertures 142, in the assembled configuration.

Alternatively, in another example, the garment insert 104 can include a grid structure 140 defining a grid array of 4 apertures arranged in a particular pattern. In this example, the garment insert 104 can be configured to transiently receive a cooling unit 102 defining a set of 4 heatsink columns 114 arranged in the particular pattern. Alternatively, in yet another example, the garment insert 104 can include a grid structure 140 defining a grid array of 16 apertures arranged in a particular pattern. In this example, the garment insert 104 can be configured to transiently receive a cooling unit 102 defining a set of 16 heatsink columns 114 arranged in the particular pattern.

6.3 Fabricating the Garment Insert

In one implementation, the garment insert 104 can be fabricated by infusing the grid receptacle 132 of the textile panel 130 with a silicone material to form the grid structure 140. In particular, in this implementation, the textile panel 130 can be fabricated by laser-cutting a fabric panel to form the set of grid receptacles 132. The grid structure 140 can be fabricated by mixing a set of silicone materials to form a silicone mixture. This silicone mixture can then be loaded into a vacuum chamber to remove air bubbles present in the silicone mixture. Additionally, the silicone mixture can be subjected to vibrations configured to further remove air bubbles from the silicone mixture. For example, the silicone mixture can be loaded into a vacuum chamber arranged on a vibrating table—such that the silicone mixture is simultaneously subjected to vacuum and vibration—for a mixing period of a fixed duration (e.g., 5 minutes).

The textile panel 130 can then be inserted within a mold (e.g., a 2-piece mold) defining a set of mold structures configured to seat within the set of grid receptacles 132 of the textile panel 130. In particular, each mold structure of the mold can define a channel grid defining a footprint matched to a target footprint of the grid structure 140. A volume of the silicone mixture can then be poured over the mold—including the textile panel 130 arranged on the mold—and settle within the channel grid of each mold structure of the mold.

For example, the mold can include: a first mold layer defining a first mold structure—in a set of mold structures corresponding to the set of grid receptacles 132—defining a grid array of column structures extending from a base surface of the first mold layer and of a column height; and a second mold layer—defining a set of mold receptacles corresponding to the set of grid receptacles 132—configured to transiently couple to the first mold layer to locate the set of mold structures of the first mold layer within the set of mold receptacles of the second mold layer in an enclosed configuration. In this example, the textile panel 130 (e.g., one or more layers of fabric) can be arranged over the first mold layer, such that the textile panel 130 seats flush against the base surface of the first mold layer and the first mold structure seats within a first grid receptacle 132—approximately flush inner walls of the first grid receptacle 132—of the textile panel 130. The second mold layer can then be arranged over the textile panel 130—interposed between the first mold layer and the second mold layer—approximately flush the textile panel 130, such that the grid array of column structures of the first mold structure extend through the first grid receptacle 132 and seat within a first aperture of the second mold layer.

The first and second mold layers can be configured to clamp sections of the textile panel 130—such as about a perimeter of each grid receptacle 132 in the set of grid receptacles 132—between the first and second mold layer to prevent infusion of the silicone mixture into these regions of the textile panel 130. The mold can therefore be configured to constrain infusion of the silicone mixture to discrete regions of the textile panel 130 bordering each grid receptacle 132 in the set of grid receptacles 132. By constraining the silicone mixture and therefore the resulting grid structures 140 to these discrete regions of the textile panel 130, the textile panel 130 can be configured to exhibit increased breathability when worn by a user. Further, the textile panel 130 can be readily integrated or sewn into a garment 150, without interference of the grid structures 140 during fabrication.

The mold—in the enclosed configuration—can then be located in the vacuum chamber, arranged on the vibrating table, for a fixed duration (e.g., 5 minutes, 7 minutes, 15 minutes) to promote removal of air bubbles from the textile panel 130 (e.g., formed of a particular fabric material) and filling of these air bubbles with the silicone material. The mold can then be removed from the vacuum chamber. Further, upon removal of the mold from the vacuum chamber, surfaces of the mold can be cleaned to remove excess silicone material—outside of the channel grid—from these surfaces prior to curing of the silicone material.

The textile panel 130 and the silicone material can then be held in the enclosed mold for a fixed curing duration (e.g., 4 hours, 12 hours, 24 hours) to cure the silicone material—loaded within the channel grid arranged within the grid receptacle 132 of the textile panel 130—within the channel grid and to inner walls of the grid receptacle 132 to form the grid structure 140. Upon expiration of the fixed curing duration, the resulting garment insert 104—including the grid structure 140 arranged within and rigidly coupled to the grid receptacle 132 of the textile panel 130—can be removed from the mold. Finally, the garment insert 104 can be cleaned to remove excess silicone material—distinct from the grid structure 140—from the garment insert 104.

In the preceding implementation, the textile panel 130 can be configured to exhibit a target porosity configured to enable infusion of the silicone material into regions of the textile panel 130—about each grid receptacle 132—to rigidly cure the grid structure 140 to the textile panel 130. For example, the textile panel 130 can be fabricated from a particular material exhibiting the target porosity. Alternatively, the textile panel 130 can be laser-cut or die-cut to include an array of pores, such that the resulting textile panel 130 exhibits the target porosity.

In one variation, the garment insert 104 can be affixed to a secondary panel—such as a fabric panel of the garment 150 and/or an additional garment insert 104—by infusing additional silicone structures to both the textile panel 130 of the garment insert 104 and the secondary panel. For example, a silicone structure—such as a rectangular structure—can be infused along a first edge of a first instance of the garment insert 104 and a second edge of a second instance of the garment insert 104 to flexibly couple the first and second of the garment insert 104 along the first and second edges. In this variation, the silicone structure can be infused to the garment insert 104 and/or the secondary panel arranged within the mold, as described above.

Alternatively, in another implementation, the garment insert 104 can be fabricated via compression molding of the silicone material—forming the grid structure 140—to a set of fabric layers (e.g., laser-cut fabric layers) forming the textile panel 130. In particular, in this implementation, the garment insert 104 can be fabricated by compressing a set of heated molds (e.g., a first and second heated mold)—loaded with a first fabric layer, a second fabric layer, and a volume of the silicone material interposed between the first fabric layer and the second fabric layer—according to a fabrication protocol defining a particular temperature and/or a particular duration. The set of heated molds can be configured to define a profile corresponding to a profile of the garment insert 104, such that the resulting garment insert 104 includes: the textile panel 130—formed of the first and second fabric layer—defining one or more grid receptacles 132; and one or more grid structures 140—formed of the volume of the silicone material—bonded to the textile panel 130 and arranged with the one or more grid receptacles 132.

However, the garment insert 104 can be fabricated via any other fabrication process, such as including compression processes, plastic injection processes, etc.

7. Cooling Unit

Generally, the wearable cooling system 100 can include a cooling unit 102—removably coupled to the garment insert 104—configured to transiently mate with the grid structure 140 to seat within the grid receptacle 132 in the assembled configuration.

In one implementation, the cooling unit 102 includes: a heatsink structure 110 defining a base section 112 and an array of heatsink columns 114 extending form the base section 112; and a polymer frame 120 rigidly coupled to the heatsink structure 110 and arranged about the base section 112. In this implementation, the array of heatsink columns 114 can be arranged in a column pattern—corresponding to the grid pattern of the grid structure 140—and can be configured to transiently seat within the grid array of apertures 142 in an assembled configuration. The polymer frame 120—arranged about the base section 112 of the heatsink structure 110—can be configured to abut surfaces of the base section 112 and inner walls of the grid receptacle 132 in the assembled configuration. In the assembled configuration, the base section 112 of the heatsink structure 110 can therefore seat within the grid receptacle 132—interposed between the grid structure 140 and the inner surface 134 of the textile panel 130 array—and the array of heatsink columns 114 can seat within (e.g., partially within) the grid receptacle 132 extending through the grid array of apertures 142.

In particular, the textile panel 130 defines an inner surface 134—configured to contact the dermal surface—and an outer surface 136 opposite the inner surface 134. Each grid structure 140—in the set of grid structures 140 integrated within the set of grid receptacles 132 of the textile panel 130—defines: an inner face 144 facing the inner surface 134 of the textile panel 130; an outer face 146—opposite the inner face 144—facing the outer surface 136 of the textile panel 130; and a grid array of apertures 142 arranged in a particular pattern. A cooling unit 102 includes a heatsink structure 110 defining: a base section 112 defining an interior surface configured to contact the dermal surface; and a set of heatsink columns 114—extending from the base section 112 opposite the interior surface—arranged in the particular pattern, such that each heatsink structure 110, in the set of heatsink structures 110, seats extending through an aperture, in the grid array of apertures 142, in the assembled configuration. The cooling unit 102 is therefore configured to insert into the grid array of apertures 142—from the inner face 144 of the grid structure 140—to transiently seat the base section 112 against the inner face 144 of the grid structure 140, within the grid receptacle 132, and locate the interior surface of the base section 112 approximately flush the inner surface 134 of the textile panel 130 in the assembled configuration.

Additionally, in one implementation, the wearable cooling system 100 can include multiple cooling units 102 removably coupled to the garment insert 104—integrated into a garment 150—and configured to cool a user wearing the garment 150. In this implementation, the wearable cooling system 100 can include a set of cooling units 102, each cooling unit 102, in the set of cooling units 102, including a heatsink structure 110 and a polymer frame 120, as described above. For example, the wearable cooling system 100 can include: a first cooling unit 102 configured to transiently insert into a grid receptacle 132 of the garment insert 104; a second cooling unit 102 configured to transiently insert into a grid receptacle 132 of the garment insert 104; a third cooling unit 102 configured to transiently insert into a grid receptacle 132 of the garment insert 104; etc.

In one example, the garment insert 104 includes the set of grid structures 140—integrated into the set of grid receptacles 132—including: a first grid structure 140 and a second grid structure 140. The first grid structure 140: spans a first grid receptacle 132 in the set of grid receptacles 132; defines a first inner face 144 facing the inner surface 134 of the textile panel 130; defines a first outer face 146 opposite the first inner face 144 and facing the outer surface 136 of the textile panel 130; and defines a first grid array of apertures 142 arranged in the first pattern. The second grid structure 140: spans a second grid receptacle 132 in the set of grid receptacles 132; defines a second inner face 144 facing the inner surface 134 of the textile panel 130; defines a second outer face 146 opposite the second inner face 144 and facing the outer surface 136 of the textile panel 130; and defines a second grid array of apertures 142 arranged in the first pattern. In this example, the set of cooling units 102 can include: a first cooling unit 102 configured to transiently seat within the first grid receptacle 132 mated with the first grid structure 140 (e.g., during a first time period); and a second cooling unit 102 configured to transiently seat within the second grid receptacle 132 mated with the second grid structure 140 (e.g., during the first time period). The garment insert 104 can therefore be configured to receive and retain both the first and second cooling units 102—within the first and second grid receptacles 132—concurrently (e.g., during the first time period), such that a user may wear the garment insert 104 (e.g., across her forehead, wrist, chest, back) loaded with both cooling units 102 in order to cool the user at a relatively increased cooling rate.

7.1 Heatsink Structure

Generally, the cooling unit 102 can include a heatsink structure 110 defining a base section 112 and an array of heatsink columns 114 extending from the base section 112, as described above.

The heatsink structure 110 can include: a substrate 116 formed of a conductive material; and a porous, hydrophilic coating 118 applied to surfaces of the conductive substrate 116. In particular, the substrate 116—formed of a conductive material (e.g., graphite)—defines: the base section 112— defining the interior surface configured to contact the dermal surface—and the set of heatsink columns 114 defining an exterior surface of the heatsink structure 110; and an open network of pores 119 extending between the interior surface and the exterior surface. The coating 118: is formed of a porous, hydrophilic material (e.g., a cementitious mixture); extends across the interior surface of the substrate 116; lines the open network of pores 119; defines a void network configured to filter hydrophobic molecules; and is configured to cooperate with the substrate 116 to wick moisture from the dermal surface, through the void network lining the open network of pores 119, and to the exterior surface, to cool the heat source.

7.2 Polymer Frame

In one implementation, the cooling unit 102 can include a polymer frame 120 arranged about the base section 112 of the heatsink structure 110. In particular, the polymer frame 120 can be rigidly coupled to (e.g., molded to) and arranged about outer walls of the base section 112. The polymer frame 120 can be configured to abut surfaces of the base section 112 and walls of the grid receptacle 132 in the assembled configuration. Therefore, the polymer frame 120 can define a frame thickness (e.g., 3 millimeters, 5 millimeters) less than a threshold thickness, such that the base section 112 and the polymer frame 120 can nest within the grid receptacle 132 in the assembled configuration.

For example, the polymer frame 120 can be: bonded to the heatsink structure 110 and arranged about a perimeter of the base section 112; and configured to abut surfaces of the base section 112 to surfaces of the grid receptacle 132 to flexibly retain the cooling unit 102 within the grid receptacle 132 in the assembled configuration.

In this implementation, the polymer frame 120 can be configured to increase durability of the cooling unit 102 by providing structural support to the heatsink structure 110. By rigidly retaining the heatsink structure 110 within a target footprint defined by the polymer frame 120, the polymer frame 120 can counteract forces applied to the heatsink structure 110 and therefore reduce damage to the heatsink structure 110 over time, such as due to breaking or separating of sections of the heatsink structure 110 outward from the target footprint. Further, by constraining the heatsink structure 110 within this target heatsink configuration or footprint, the polymer frame 120 can be configured to extend a shelf life of the cooling unit 102, such as regardless of damage (e.g., breaks, chips) in the heatsink structure 110.

In one implementation, the polymer frame 120 can be fabricated from a flexible material. For example, the polymer frame 120 can be fabricated from a polycaprolactone (or "PCL") material. Additionally and/or alternatively, in another implementation, the polymer frame 120 can be fabricated from a rigid material (e.g., a rigid plastic).

In one example, the cooling unit 102 includes a heatsink structure 110 including: a substrate 116 formed of a graphite material (e.g., a graphite foam) exhibiting a target conductivity and a target durability; and a coating 118 formed of a hydrophilic, cementitious mixture of water and cement extending across the interior surface of the substrate 116 and lining the open network of pores 119 of the substrate 116. In this example, the cooling unit 102 can further include a polymer frame 120: formed of a polycaprolactone material and exhibiting a target flexibility; bonded to the heatsink structure 110 and arranged about a perimeter of the base section 112; and configured to abut surfaces of the base section 112 to surfaces of the grid receptacle 132 to flexibly retain the cooling unit 102 within the grid receptacle 132 in an assembled configuration. Furthermore, in this example, each grid structure 140, in the set of grid structures 140 of the garment insert 104 can be formed of a silicone material and configured to contour about the dermal surface, such as about a forehead, wrist, or chest of a human user wearing the garment insert 104.

7.3 Fabricating the Cooling Unit: Polymer Frame+Heatsink Structure

In one implementation, the cooling unit 102 can be fabricated by molding a polymer frame 120 (e.g., a PCL frame) about the base section 112 of the heatsink structure 110.

In this implementation, the polymer frame 120 can initially be fabricated via 3-d printing or injection molding. The resulting polymer frame 120 can then be arranged about a perimeter of the base section 112 of the heatsink structure 110, such as by stretching the flexible, polymer frame 120 around the perimeter.

The cooling unit 102 can then be located within a frame mold (e.g., a silicone mold). In particular, the frame mold can define a bottom surface, an upper surface opposite the bottom surface, and a recess integrated into the upper surface and defining a recess depth approximating a height of the base section 112 of the heatsink structure 110. The base section 112 of the heatsink structure 110—including the polymer frame 120 arranged about the perimeter—can therefore seat within the recess of the frame mold in order to couple the cooling unit 102 to the frame mold, with the array of heatsink columns 114 extending upward from the base section 112 above the upper surface of the frame mold. The frame mold-loaded with the heatsink structure 110 and the polymer frame 120—can then be located on a heated surface (e.g., a hot plate), at a target temperature and over a target heating duration, in order to melt the polymer frame 120 within the recess. Then, in response to expiration of the target heating duration, the frame mold can be removed from the heated surface and cooled to room temperature—in order to cool and solidify the melted polymer frame 120 about the base section 112 within the recess of the frame mold—over a target cooling duration. Then, upon expiration of the target cooling duration, the cooling unit 102 can be removed from the frame mold.

Upon removal of the cooling unit 102 from the frame mold, the cooling unit 102 can be reheated to enable sculpting and/or molding of surfaces of the cooling unit 102 for removal of imperfections during a finishing period. For example, during the finishing period, the cooling unit 102 can be reheated to melt the polymer frame 120 and a user may manually remove excess PCL material and shape the polymer frame 120 (e.g., via a silicone spatula or scraper) accordingly.

In this implementation, the frame mold can be formed of a deformable material (e.g., a silicone material) configured to exert a threshold force on the polymer frame 120—during heating of the polymer frame 120 within the frame mold—to drive the polymer frame 120 against the heatsink structure 110 and therefore increase adhesion between the polymer frame 120 and the heatsink structure 110. Further, the polymer frame 120 can be configured to exhibit a glass transition temperature less than a threshold glass transition temperature, in order to minimize high-temperature cycling of the heatsink structure 110 during molding of the polymer frame 120 to the heatsink structure 110, and therefore minimize damage to the coating 118 of the heatsink structure 110. For example, the polymer frame 120 can be formed of a PCL material exhibiting a glass transition temperature of approximately 60 degrees Celsius.

However, the polymer frame 120 can be molded and/or bonded to the heatsink structure 110 via any other bonding process.

7.4 Variation: Moisture & Air Supply

In one variation, the wearable cooling system 100 can include a water supply 160 configured to supply volumes of water to the set of cooling units 102—transiently installed within the set of grid receptacles 132 of the garment insert 104—to increase a rate of moisture evaporation from surfaces of the set of heatsink structures 110 and therefore increase a rate of cooling of a human user (e.g., at the dermal surface) wearing the garment insert 104. In particular, in this variation, the wearable cooling system 100 can leverage moisture-supplied by the water supply 160 integrated within a garment 150 including the garment insert 104—in addition to human sweat at the dermal surface to cool the dermal surface and/or the human user via evaporative cooling.

In one example, the wearable cooling system 100 can include: a water supply 160 configured to transiently store a volume of water; and a set of fluid channels 148 fluidly coupled to the water supply 160 and extending through the set of grid structures 140. In this example, each grid structure 140, in the set of grid structures 140, can define an array of pores configured to transiently release water from fluid channels 148—in the set of fluid channels 148 extending through the grid structure 140—toward surfaces of a cooling unit 102 and/or a heatsink structure 110 of the cooling unit 102, mated with the grid structure 140, in order to wet surfaces of the heatsink structure 110 and thereby promote evaporation of this moisture (e.g., water) from surfaces of the heatsink structure 110, thereby cooling the human user wearing the garment 150.

Additionally or alternatively, in another variation, the wearable cooling system 100 can be configured to increase airflow across the set of cooling units 102 (transiently) installed within the set of grid receptacles 132 of the garment insert 104. In particular, in this variation, the wearable cooling system 100 can include a blower (e.g., a manual or automatic blower) configured to direct airflow across the set of cooling units 102—such as in addition to ambient airflow—in order to increase a rate of moisture evaporative from the set of heatsink structures 110 and, thereby, increase a cooling rate of the dermal surface and the human user wearing the garment insert 104.

For example, the garment insert 104 can be integrated into a garment 150 including a blower (e.g., a fan, an air-propelling device)—integrated into the garment insert 104 and/or the garment 150—including a user control configured to trigger blowing of air across the set of cooling units 102 responsive to actuation of the user control by the human user. In particular, the human user may actuate the user control-such as by compressing an inflated tab containing a volume of air—to trigger blowing of air (e.g., from within the inflated tab) across the set of cooling units 102 and, thereby, increase a rate of moisture evaporation from surfaces of the set of heatsink columns 114 into air blowing across the set of cooling units 102. The wearable cooling system 100 can therefore continue cooling the user-via actuation of the blower-when ambient airflow is relatively low, such as when the user is stationary and/or on when the user exercises outdoors on a relatively windless day.

Additionally, in the preceding example, the garment 150 can include fabric and/or other material extending across the set of heatsink structures 114 and/or base sections 112 of the set of cooling units 102—transiently seated within the set of grid receptacles 132 of the textile panel 130—to promote airflow across the set of heatsink structures 114 and prevent air from flowing outward and/or away from an airflow pathway extending across the set of heatsink structures 114. In this example, the cooling units 102 may absorb relatively less moisture from the dermal surface due to additional fabric or material forming a barrier between the dermal surface and the set of cooling units 102. Therefore, in this example, the wearable cooling system 100 can further include the water supply 160 and the set of fluid channels 148 fluidly coupled to the water supply 160 and extending through the set of grid structures 140 of the garment insert 104, as described above. Each grid structure 140, in the set of grid structures 140, can define an array of pores configured to transiently release water from fluid channels 148—in the set of fluid channels 148 extending through the grid structure 140—toward surfaces of a heatsink structure 110 of the cooling unit 102, mated with the grid structure 140, in order to wet surfaces of the heatsink structure 110 and thereby promote evaporation of this moisture, thus cooling the human user wearing the garment 150.

8. Re-Configurable Cooling Units

In one implementation, the set of cooling units 102 can be configured to transiently couple to the garment insert 104 in various configurations over time. In particular, in this implementation, each cooling unit 102, in the set of cooling units 102, can be configured to install within different grid receptacles 132—each defining a particular position within the garment insert 104—of the garment insert 104 over time.

For example, the garment insert 104 can include the set of grid structures 140—integrated into the set of grid receptacles 132—including a first grid structure 140 and a second grid structure 140. In this example, the first grid structure 140: spans a first grid receptacle 132 in the set of grid receptacles 132; defines a first inner face 144 facing the inner surface 134 of the textile panel 130; defines a first outer face 146 opposite the first inner face 144 and facing the outer surface 136 of the textile panel 130; and defines a first grid array of apertures 142 arranged in the first pattern. The second grid structure 140: spans a second grid receptacle 132 in the set of grid receptacles 132; defines a second inner face 144 facing the inner surface 134 of the textile panel 130; defines a second outer face 146 opposite the second inner face 144 and facing the outer surface 136 of the textile panel 130; and defines a second grid array of apertures 142 arranged in the first pattern. In this example, the set of cooling units 102 can include a first cooling unit 102 configured to: transiently seat within the first grid receptacle 132—mated with the first grid structure 140—during a first time period; and transiently seat within the second grid receptacle 132—mated with the second grid structure 140—during a second time period (e.g., preceding or succeeding the first time period). The first cooling unit 102 can therefore be configured to install in any one of the grid receptacles 132, in the set of grid receptacles 132, such that the user may adjust a position of the first cooling unit 102 within the garment insert 104 over time.

In another example, the textile panel 130 can define: a first grid receptacle 132 including a first grid structure 140 arranged within the first grid receptacle 132; a second grid receptacle 132 including a second grid structure 140 arranged within the second grid receptacle 132; and a third grid receptacle 132 including a third grid structure 140 arranged within the third grid receptacle 132. In this example, during a first time period, the wearable cooling system 100 can include: a first cooling unit 102 mating with the first grid structure 140 arranged within the first grid receptacle 132; and a second cooling unit 102 mating with the second grid structure 140 arranged within the second grid receptacle 132. Later, during a second time period, the wearable cooling system 100 can include: the first cooling unit 102 mating with the first grid structure 140 arranged within the first grid receptacle 132; and the second cooling unit 102 mating with the third grid structure 140 arranged within the third grid receptacle 132. Later, during a third time period, the wearable cooling system 100 can include: the first cooling unit 102 mating with the first grid structure 140 arranged within the first grid receptacle 132; the second cooling unit 102 mating with the second grid structure 140 arranged within the second grid receptacle 132; and a third cooling unit 102 mating with the third grid structure 140 arranged within the third grid receptacle 132.

The set of cooling units 102 can therefore be reassembled (e.g., by the user) in various configurations within the garment insert 104 over time. By enabling modification of this configuration or arrangement of cooling units 102 within the garment insert 104, the wearable cooling system 100 can enable the user to locate the set of cooling units 102 in a configuration corresponding to a profile (e.g., curvature, size) of the target dermal surface (e.g., forehead, forearm, chest, lower back) of this particular user. In particular, the user may arrange the set of cooling units 102 within the flexible unit in a particular configuration-corresponding to the profile of the target dermal surface of the user—in order to maximize contact area between the set of cooling units 102 and the target dermal surface.

For example, the wearable cooling system 100 can include a garment insert 104—including a linear row of 8 grid receptacles 132—integrated into an arm band. At a first time, a user may insert each cooling unit 102, in a set of 8 cooling units 102, within a grid receptacle 132, in the linear row of 8 grid receptacles 132, in a first assembled configuration. The user may then wear the arm band about her upper arm in the first assembled configuration. However, based on a size (e.g., circumference) of the user's upper arm, the set of 8 cooling units 102 can exhibit a relatively small total contact area between cooling units 102 and the surface of the upper arm, as contact between adjacent heatsink structure 110 prevents further bending or contouring of the garment insert 104 about the surface of the user's upper arm. Therefore, the user may: remove the arm band from her upper arm; remove 4 cooling units 102, in the set of 8 cooling units 102, from the set of grid receptacles 132—such as from every other grid receptacle 132 in the linear row—in order to increase distance between adjacent cooling units 102 loaded in the garment insert 104; and relocate the arm band about her upper arm in a second configuration. In the second configuration, the remaining cooling units 102 (e.g., 4 cooling units 102) can exhibit a greater total contact area between cooling units 102 and the surface of the upper arm, as the garment insert 104 can bend about the surface with limited or no contact between adjacent heatsink structures 110 in the garment insert 104.

Therefore, by enabling a user to rapidly insert and remove cooling units 102 from grid receptacles 132 of the garment insert 104, the wearable cooling system 100 can enable tailoring of cooling unit 102 configurations to this particular user, such as based on user comfort and maximizing contact area between cooling units 102 and dermal surfaces of the user.

Furthermore, over time, the user may replace a first cooling unit 102—installed within a particular grid receptacle 132 of the garment insert 104—with a second cooling unit 102 in order to minimize reduction in cooling rate due to deterioration or damage of the first cooling unit 102 over time and/or in order to modify the cooling rate, such as based on a size difference between the first and second cooling units 102. For example, the garment insert 104 can include a first grid structure 140: spanning a first grid receptacle 132 in the set of grid receptacles 132; defining a first inner face 144 facing the inner surface 134 of the textile panel 130; defining a first outer face 146 opposite the first inner face 144 and facing the outer surface 136 of the textile panel 130; and defining a first grid array of apertures 142 arranged in the first pattern. In this example, the set of cooling units 102 can include: a first cooling unit 102 configured to transiently seat within the first grid receptacle 132—mated with the first grid structure 140—during a first time period; and a second cooling unit 102 configured to transiently seat within the first grid receptacle 132—mated with the first grid structure 140—during a second time period succeeding the first time period, such that the user may install the second cooling unit 102 within the first grid receptacle 132 in replacement of the first cooling unit 102.

8.1 Variation: Cooling Unit Type

In one variation, the wearable cooling system 100 can include a suite of cooling units 102 of various cooling unit 102 types. For example, the suite of cooling units 102 can include sets of cooling units 102 of different cooling unit 102 types, such as different sizes (e.g., height, cross-section), shapes, target cooling rates, etc.

In one implementation, the wearable cooling system 100 can include a suite of cooling units 102 of variable target cooling rates. In particular, in this implementation, the wearable cooling system 100 can include: a first set of cooling units 102 configured to exhibit a first target cooling rate; and a second set of cooling units 102 configured to exhibit a second target cooling rate exceeding the first target cooling rate. A user may therefore selectively couple: the first set of cooling units 102 to the set of grid receptacles 132 to achieve the first target cooling rate; the second set of cooling units 102 to the set of grid receptacles 132 to achieve the second target cooling rate; and/or a subset of cooling units 102 from the first set of cooling units 102 and a subset of cooling units 102 from the second set of cooling units 102 to the set of grid receptacles 132 to achieve a third target cooling rate exceeding the first target cooling rate and falling below the second target cooling rate. In one example, a user may: couple a first cooling unit 102—defining a first cooling rate—to a grid structure 140 in a garment insert 104 integrated within her headband in preparation for running outside on a first day exhibiting relatively moderate-temperature weather; and remove the first cooling unit 102 from the grid structure 140, and insert a second cooling unit 102—defining a second cooling rate exceeding the first cooling rate-into the grid structure 140 in preparation for running outside on a second day exhibiting relatively high-temperature weather. In this example, the wearable cooling system 100 can therefore: cool the user—by wicking moisture (e.g., sweat) from the user's forehead—at the first cooling rate while the user wears the headband running on the first day; and then cool the user at the increased second cooling rate while the user wears the headband running on the second day.

In one example, the set of cooling units 102 can include a first cooling unit 102 including a first heatsink structure 110: including a first base section 112 defining a first interior surface configured to contact the dermal surface; including a first set of heatsink columns 114—each heatsink column, in the first set of heatsink columns 114, configured to seat extending through an aperture in the grid array of apertures 142—of a first size, extending from the first base section 112 opposite the first interior surface, arranged in the second pattern corresponding to the first pattern of the grid array of apertures 142 of the grid structure 140; and configured to wick moisture from the dermal surface toward surfaces of the first set of heatsink columns 114 to cool the dermal surface—and the corresponding heat source (e.g., a human wearing the first cooling unit 102 across the dermal surface) at a first rate corresponding to the first size.

Additionally, in the preceding example, the set of cooling units 102 can further include a second cooling unit 102 including a second heatsink structure 110: including a second base section 112 defining a second interior surface configured to contact the dermal surface; including a second set of heatsink columns 114—each heatsink column, in the second set of heatsink columns 114, configured to seat extending through an aperture in the grid array of apertures 142—of a second size exceeding the first size, extending from the second base section 112 opposite the second interior surface, arranged in the second pattern corresponding to the first pattern of the grid array of apertures 142 of the grid structure 140; and configured to wick moisture from the dermal surface toward surfaces of the second set of heatsink columns 114 to cool the dermal surface—and the corresponding heat source—at a second rate exceeding the first rate and corresponding to the second size.

In this example, the wearable cooling system 100 can therefore include cooling units 102 including heatsink columns 114 of varying size (e.g., length, height, surface area) and configured to cool the user-wearing the garment insert 104 loaded with these cooling units 102—at varying rates corresponding to (e.g., proportional) a size of the heatsink columns 114.

Additionally, in this variation, the wearable cooling system 100 can include cooling units 102 of a variety of colors corresponding to different types of cooling units 102. For example, the wearable cooling system 100 can include: a first cooling unit 102 defining a first target cooling rate and including a coating-applied to a first heatsink structure 110—of a first color (e.g., blue) linked to the first target cooling rate; a second cooling unit 102 defining a second target cooling rate and including a coating-applied to a second heatsink structure 110—of a second color (e.g., green) linked to the second target cooling rate; and/or a third cooling unit 102 defining a third target cooling rate and including a coating-applied to a third heatsink structure 110—of a third color (e.g., yellow) linked to the third target cooling rate. Additionally and/or alternatively, in another example, each cooling unit 102 can include a polymer frame 120 of a particular color corresponding to the type of cooling unit 102. Additionally and/or alternatively, in yet another example, the wearable cooling system 100 can include grid structures 140 of a variety of colors and/or configured to receive different types of cooling units 102.

9. Variation: Multiple Garment Types

In one variation, the wearable cooling system 100 can include a suite of garment inserts 104 integrated into garments 150 of various garment 150 types. In this variation, each garment insert 104, in the suite of garment inserts 104, can include a set of grid receptacles 132 configured to transiently receive and retain a set of cooling units 102 within the garment insert 104. For example, the wearable cooling system 100 can include: a first garment insert 104—configured to be worn across a human forehead—integrated into a headband and defining a first set of grid receptacles 132; a second garment insert 104—configured to be worn across a human back—integrated into a vest and defining a second set of grid receptacles 132; and a third garment insert 104—configured to be worn across a human forearm—integrated into a wristband and defining a third set of grid receptacles 132. In this example, the wearable cooling system 100 can further include a set of cooling units 102 configured to: transiently mate with the first set of grid receptacles 132 to cool a forehead of the user wearing the headband; transiently mate with the second set of grid receptacles 132 to cool a back of a user wearing the vest; and transiently mate with the third set of grid receptacles 132 to cool an arm of the user wearing the armband.

In this example, a user may therefore leverage this single set of cooling units 102 to selectively cool various regions of the user's body by coupling the set of cooling units 102 to a particular garment insert 104—integrated to the headband, vest, and/or armband-such as in preparation for a particular activity. Over time, the user may purchase additional garment inserts 104—integrated into various garments 150 types—for combining with this set of cooling units 102. The user may therefore purchase instances of the garment insert 104 and instances of the set of cooling units 102 separately and/or concurrently based on the user's individual preferences.

10. Variation: Rigid Inserts

In one variation, the wearable cooling system 100 can include a set of rigid inserts 170 integrated within the garment insert 104 and arranged about the set of grid receptacles 132.

In particular, in this variation, the garment insert 104 is integrated into a garment configured to be worn across and/or about a dermal surface of a human body, such as about a wrist, leg, forehead, upper arm, chest, neck, etc.

The wearable cooling system 100 can therefore incorporate the set of rigid inserts 170 within the garment insert 104 in order to distribute a tensile force-applied during wearing of the garment 150 about the dermal surface-across the set of rigid inserts 170, thereby maximizing durability of the wearable cooling system 100 and minimizing deformation of the textile panel 130 and the set of grid structures 140 (e.g., formed of silicone). For example, the wearable cooling system 100 can include: a first rigid insert 170 integrated into a first side of the garment insert 104, along a length of the textile panel 130 and adjacent a first column of grid structures 140 in the set of grid structures 140; and a second rigid insert 170 integrated into a second side of the garment insert 104—opposite the first side-along a length of the textile panel 130 and adjacent a second column of grid structures 140 in the set of grid structures 140.

In one implementation, each rigid insert 170: is integrated into a particular side of the garment insert 104—arranged along a length of a first side of the textile panel 130—adjacent a first column of grid structures 140 in the set of grid structures 140; defines a target profile-such as defining and/or less than a target thickness (e.g., 1 millimeter, 3 millimeters) configured to minimize a thickness of the garment insert 104 and enable the garment insert 104 to seat approximately flush across the dermal surface; and defines a coupling feature configured to receive and/or couple an attachment element (e.g., a strap) configured to transiently locate and affix the garment 150 about the dermal surface of the user. The rigid insert 170 can therefore be configured to receive and/or distribute a tensile force applied to the garment insert 104 by the attachment element during application and/or wearing of the garment insert 104 about and/or across the dermal surface. In one example, the rigid insert 170 can be formed of a plastic material (e.g., polypropylene).

Figure 9:
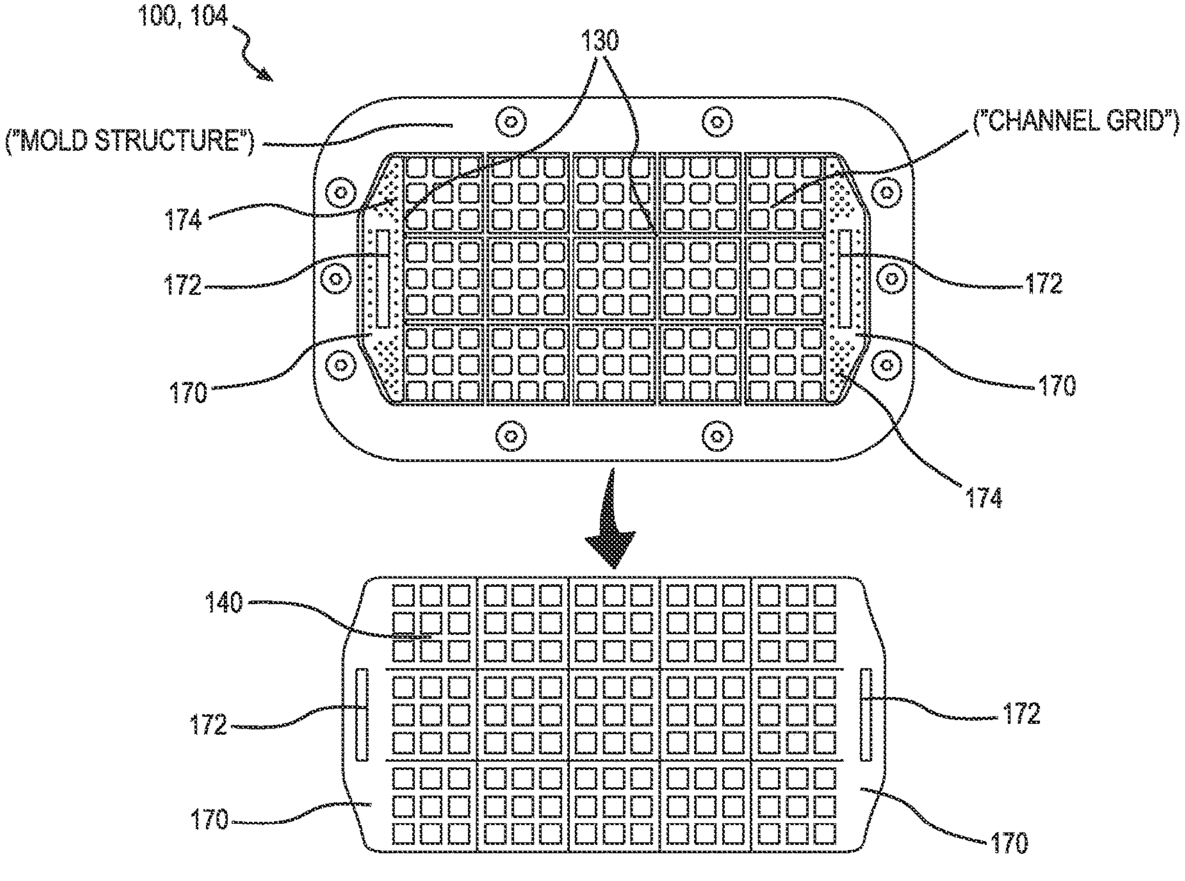
FIG. 9 is a schematic representation of one variation of the wearable cooling system 100.

Additionally, in one implementation, as shown in FIG. 9, each rigid insert 170 can define an array of holes 174 extending through the rigid insert 170 and configured to be filled with the silicone material-forming the set of grid structures 140—during manufacturing of the garment insert 104 in order to increase adhesion of the silicone material to the rigid insert 170. In particular, in this implementation, during molding of the silicone material to the textile panel 130 to form the set of grid structures 140 and the resulting garment insert 104, the silicone material can further be molded to sides of the textile panel 130—extending outward from the set of grid structures 140—and to the set of rigid inserts 170 arranged over these sides of the textile panel 130. The silicone material therefore forms a silicone structure forming the set of grid structures 140 and encapsulating the set of rigid inserts 170. The set of rigid inserts 170 is therefore embedded in this silicone structure and bonded to the sides of the textile panel 130.

11. Variation: Attachment Element

In one variation, the wearable cooling system 100 can include an attachment element 180 configured to affix the garment insert 104 to a dermal surface of the user.

In one implementation, the attachment element 180 defines a strap 180 configured to transiently couple to the garment insert 104 to transiently affix the garment insert 104 to the dermal surface. In particular, in this implementation, the wearable cooling system 100 can include: a strap 180; the set of rigid inserts 170—integrated within the garment insert 104 and arranged about the set of grid receptacles 132 (e.g., as described above)—configured to transiently engage the strap 180 to couple the strap 180 to the garment insert 104 and distribute a tensile force applied by the strap 180 across the set of rigid inserts 170 to minimize deformation of the textile panel 130 and the set of grid structures 140 when the wearable cooling system 100 is worn by the user across the dermal surface.

Figure 8:
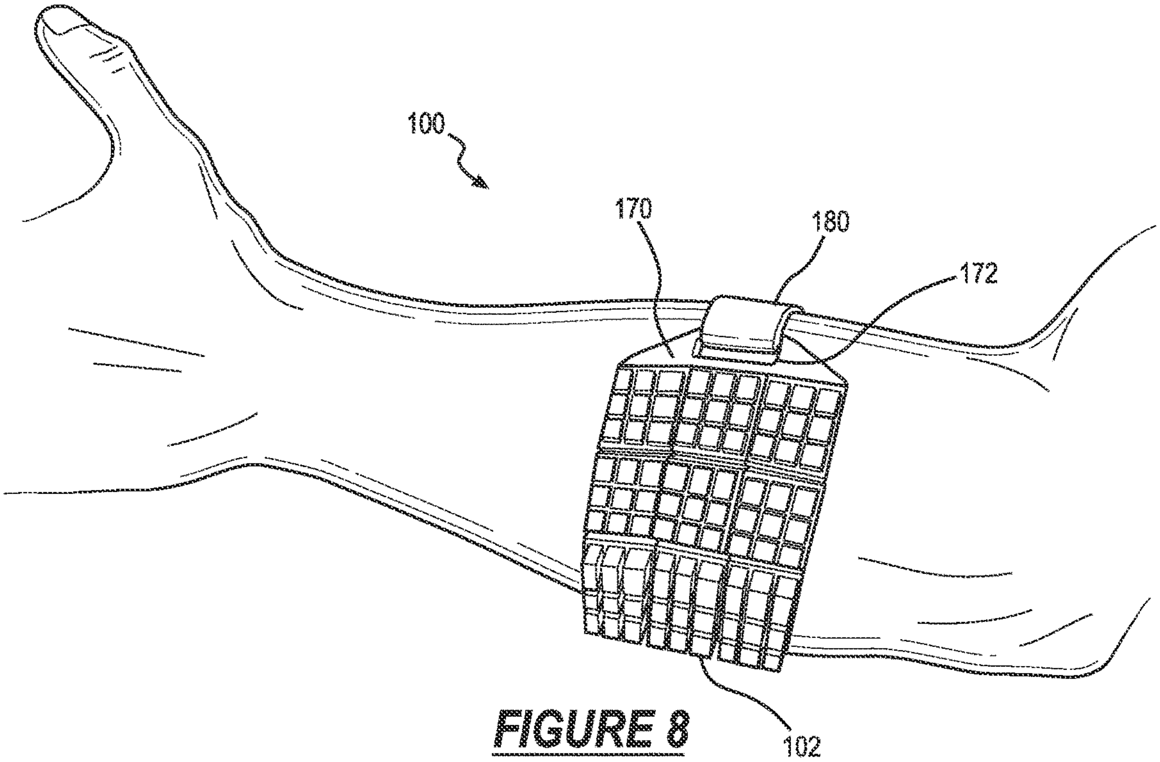
FIG. 8 is a schematic representation of one variation of the wearable cooling system.
Figure 10:
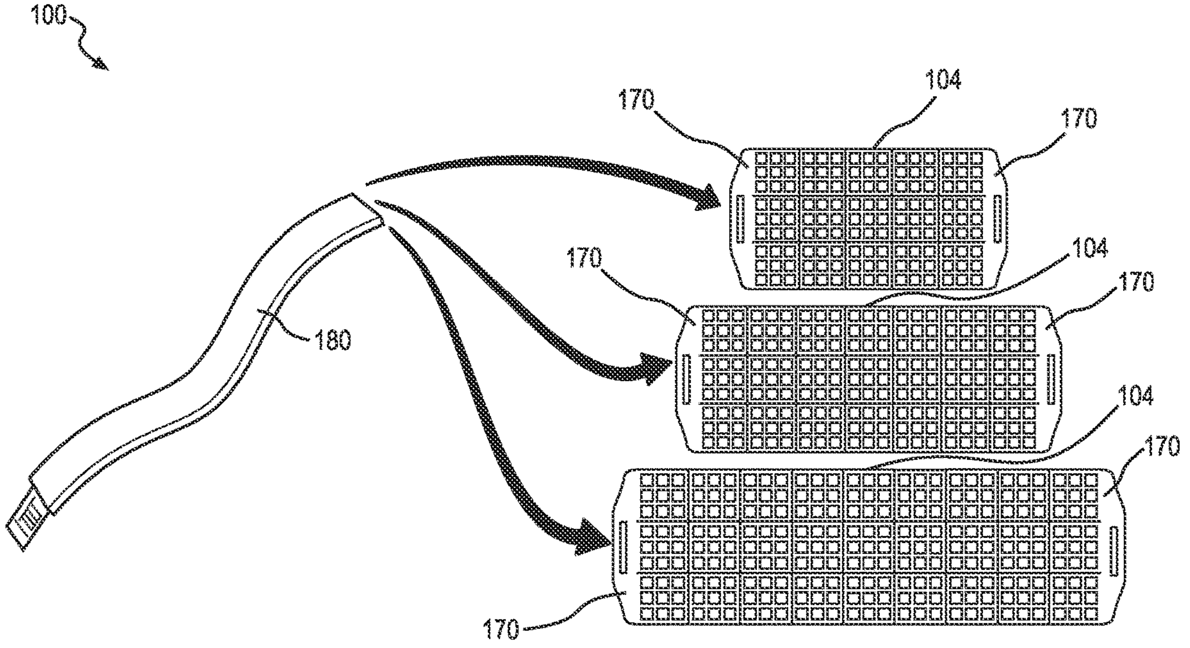
FIG. 10 is a schematic representation of one variation of the wearable cooling system.

In one example, as shown in FIGS. 8 and 10, the garment insert 104 can include a set of rigid inserts 170 including: a first rigid insert 170 integrated into a first side of the garment insert 104, along a length of the textile panel 130 and adjacent a first column of grid structures 140 in the set of grid structures 140; and a second rigid insert 170 integrated into a second side of the garment insert 104—opposite the first side—along a length of the textile panel 130 and adjacent a second column of grid structures 140 in the set of grid structures 140. Each rigid insert 170, in the set of rigid inserts 170, can define an insert aperture 172 configured to transiently receive an end of the strap 180—such that the strap 180 loops through the aperture—to transiently couple the strap 180 to the garment insert 104. The first and second rigid inserts 170 can therefore cooperate to receive a force applied by the strap 180 (e.g., during wearing of the wearable cooling system 100 by a user) to the garment insert 104 and reduce a tensile force applied to the textile panel 130—such as including silicone material bonded to sections of a fabric panel—and/or the set of grid structures 140.

Additionally, in one variation, the wearable cooling system 100 can include a suite of straps 180 of various sizes and/or profiles configured to enable wearing of the garment insert 104 across dermal surfaces of various sizes and/or shapes.

For example, the wearable cooling system 100 can include: a first strap 180 of a first length—configured to transiently couple to the garment insert 104 via insert apertures 172 of the set of rigid inserts 170—configured to be worn about human wrists of circumferences within a first circumference range; and a second strap 180 of a second length—configured to transiently couple to the garment insert 104 via insert apertures 172 of the set of rigid inserts 170—configured to be worn about human wrists of circumferences within a second circumference range, circumferences within the second circumference range exceeding the first circumference range. Therefore, a first user—with a wrist of a first circumference falling within the first circumference range—may couple the first strap 180 to the garment insert 104 and wear the wearable cooling system 100 about her wrist accordingly. Additionally, a second user—with a wrist of a second circumference falling within the second circumference range—may couple the second strap 180 to the garment insert 104 and wear the wearable cooling system 100 about her wrist accordingly.

In another example, the wearable cooling system 100 can include: a first strap 180 of a first profile—configured to transiently couple to the garment insert 104 via insert apertures 172 of the set of rigid inserts 170—corresponding to an average wrist profile (e.g., wrist shape, wrist contour, wrist size) of a human and configured to be worn about a wrist; and a second strap 180 of a second profile—configured to transiently couple to the garment insert 104 via insert apertures 172 of the set of rigid inserts 170—corresponding to an average chest profile (e.g., chest shape, chest contour, chest size) of a human and configured to be worn about a chest. Therefore, at a first time, a user may couple the first strap 180 to the garment insert 104 and wear the wearable cooling system 100 about her wrist accordingly. Later, the user may couple the second strap 180 to the garment insert 104—in replacement of the first strap 180—and wear the wearable cooling system 100 about her chest accordingly. In this example, the wearable cooling system 100 can similarly include additional straps 180 configured to be worn about an upper arm, a leg, a forehead, a neck, etc.

As a person skilled in the art will recognize from the previous detailed description and from the figures and claims, modifications and changes can be made to the embodiments of the invention without departing from the scope of this invention as defined in the following claims.

I claim:

1. A wearable cooling system comprising:
- a garment insert configured to be worn across a dermal surface and comprising:
  - a textile panel defining:
    - an inner surface configured to contact the dermal surface;
    - an outer surface opposite the inner surface; and
    - a set of grid receptacles, each grid receptacle, in the set of grid receptacles, extending between the inner surface and the outer surface; and
    - a set of grid structures, each grid structure, in the set of grid structures:
    - rigidly arranged within and spanning a grid receptacle in the set of grid receptacles;
    - formed of a flexible material; and
    - defining:
      - an inner face facing the inner surface of the textile panel;
      - an outer face opposite the inner face and facing the outer surface of the textile panel; and
      - a grid array of apertures arranged in a first pattern and extending between the inner face and the outer face of the grid structure; and
- a set of cooling units, each cooling unit in the set of cooling units:
  - configured to transiently mate with a grid structure, in the set of grid structures, to seat within a corresponding grid receptacle, in the set of grid receptacles, defining a corresponding grid array of apertures; and comprising a heatsink structure:

formed of a rigid material comprising a porous structure;

defining:

a base section defining:

an interior surface configured to contact the dermal surface; and an outer base surface configured to seat against the inner face of the grid structure; and a set of heatsink columns:

extending from the outer base surface of the base section;

arranged in a second pattern complementary to the first pattern; and configured to seat extending through the corresponding grid array of apertures to transiently retain the cooling unit within the grid receptacle; and configured to wick moisture through the porous structure from the dermal surface toward surfaces of the set of heatsink columns to cool the dermal surface; and comprising a polymer frame arranged about a perimeter of the base section and configured to abut surfaces of the base section to surfaces of the grid receptacle to flexibly retain the cooling unit within the grid receptacle.

2. The wearable cooling system of claim 1, wherein the polymer frame is:

formed of a second flexible material;

bonded to the heatsink structure and arranged about the perimeter of the base section; and configured to abut surfaces of the base section to surfaces of the grid receptacle to flexibly retain the cooling unit within the grid receptacle in an assembled configuration.

3. The wearable cooling system of claim 2:

wherein the polymer frame:

is formed of a second flexible material; and defines a first cross-section corresponding to a second cross-section of the grid receptacle and is configured to nest within the grid receptacle to locate the cooling unit within the assembled configuration.

4. The wearable cooling system of claim 1, wherein the cooling unit is configured to insert into the grid array of apertures, from the inner face of the grid structure, to transiently seat the base section against the inner face of the grid structure within the grid receptacle and locate the interior surface of the base section approximately flush the inner surface of the textile panel in an assembled configuration.

5. The wearable cooling system of claim 1, wherein the heatsink structure comprises:

a substrate defining:

the base section and the set of heatsink columns defining an exterior surface of the heatsink structure; and an open network of pores extending between the interior surface of the base section and the exterior surface of the set of heatsink columns; and a coating:

formed of a porous, hydrophilic material;

extending across the interior surface of the substrate;

lining the open network of pores;

defining a void network configured to filter hydrophobic molecules; and configured to cooperate with the substrate to wick moisture from the dermal surface, through the void network lining the open network of pores, and to the exterior surface, to cool the dermal surface.

6. The wearable cooling system of claim 5:

wherein the grid structure is formed of a silicone material and configured to contour about the dermal surface;

wherein the substrate is formed of a graphite material exhibiting a target conductivity and a target durability;

wherein the coating is formed of a cementitious mixture of water and cement; and wherein each cooling unit, in the set of cooling units, further comprises a polymer frame:

formed of a polycaprolactone material and exhibiting a target flexibility;

bonded to the heatsink structure and arranged about a perimeter of the base section; and configured to abut surfaces of the base section to surfaces of the grid receptacle to flexibly retain the cooling unit within the grid receptacle in an assembled configuration.

7. The wearable cooling system of claim 1:

wherein the garment insert is integrated into a headband configured to be worn across a forehead of a human user;

wherein the inner surface of the textile panel is configured to contact the forehead; and wherein the heatsink structure is configured to wick moisture from the forehead toward surfaces of the set of heatsink columns to cool the human user.

8. The wearable cooling system of claim 1:

wherein the garment insert is integrated into an armband configured to be worn across a forearm of a human user;

wherein the inner surface of the textile panel is configured to contact the forearm; and wherein the heatsink structure is configured to wick moisture from the forearm toward surfaces of the set of heatsink columns to cool the human user.

9. The wearable cooling system of claim 1:

wherein the set of grid structures comprises:

a first grid structure:

spanning a first grid receptacle in the set of grid receptacles;

defining a first inner face facing the inner surface of the textile panel;

defining a first outer face opposite the first inner face and facing the outer surface of the textile panel; and defining a first grid array of apertures arranged in the first pattern; and a second grid structure:

spanning a second grid receptacle in the set of grid receptacles;

defining a second inner face facing the inner surface of the textile panel;

defining a second outer face opposite the second inner face and facing the outer surface of the textile panel; and defining a second grid array of apertures arranged in the first pattern; and wherein the set of cooling units comprises:

a first cooling unit transiently seated within the first grid receptacle, mated with the first grid structure, during a first time period; and a second cooling unit transiently seated within the second grid receptacle, mated with the second grid structure, during the first time period.

10. The wearable cooling system of claim 1:

wherein the set of grid structures comprises a first grid structure:

spanning a first grid receptacle in the set of grid receptacles;

defining a first inner face facing the inner surface of the textile panel;

defining a first outer face opposite the first inner face and facing the outer surface of the textile panel; and defining a first grid array of apertures arranged in the first pattern; and wherein the set of cooling units comprises:

a first cooling unit transiently seated within the first grid receptacle, mated with the first grid structure, during a first time period; and a second cooling unit transiently seated within the first grid receptacle, mated with the first grid structure, during a second time period succeeding the first time period.

11. The wearable cooling system of claim 1:

wherein the set of grid structures comprises:

a first grid structure:

spanning a first grid receptacle in the set of grid receptacles;

defining a first inner face facing the inner surface of the textile panel;

defining a first outer face opposite the first inner face and facing the outer surface of the textile panel; and defining a first grid array of apertures arranged in the first pattern; and a second grid structure:

spanning a second grid receptacle in the set of grid receptacles;

defining a second inner face facing the inner surface of the textile panel;

defining a second outer face opposite the second inner face and facing the outer surface of the textile panel; and defining a second grid array of apertures arranged in the first pattern; and wherein the set of cooling units comprises a first cooling unit transiently configured to:

transiently seat within the first grid receptacle, mated with the first grid structure, during a first time period; and transiently seat within the second grid receptacle, mated with the second grid structure, during a second time period succeeding the first time period.

12. The wearable cooling system of claim 1, wherein the set of cooling units comprises a first cooling unit comprising a first heatsink structure:

comprising a first base section defining:

a first interior surface configured to contact the dermal surface; and a first outer base surface opposite the first interior surface;

comprising a first set of heatsink columns: of a first size:

of a first size;

extending from the first outer base surface of the first base section;

arranged in the second pattern complementary to the first pattern; and configured to seat extending through in the corresponding grid array of apertures; and configured to wick moisture from the dermal surface toward surfaces of the first set of heatsink columns to cool the dermal surface at a first rate corresponding to the first size.

13. The wearable cooling system of claim 12, wherein the set of cooling units comprises a second cooling unit comprising a second heatsink structure:

comprising a second base section defining:

a second interior surface configured to contact the dermal surface; and a second outer base surface opposite the first interior surface;

comprising a second set of heatsink columns:

of a second size exceeding the first size;

extending from the second outer base surface of the base section;

arranged in the second pattern complementary to the first pattern; and configured to seat extending through in the corresponding grid array of apertures; and configured to wick moisture from the dermal surface toward surfaces of the second set of heatsink columns to cool the dermal surface at a second rate corresponding to the second size, the second rate exceeding the first rate.

14. The wearable cooling system of claim 1:

further comprising:

a water supply configured to transiently store a volume of water; and a set of fluid channels:

fluidly coupled to the water supply; and extending through the set of grid structures; and wherein each grid structure, in the set of grid structures, defines an array of pores configured to transiently release water from fluid channels, in the set of fluid channels, extending through the grid structure, toward surfaces of a cooling unit, in the set of cooling units, mated with the grid structure to wet the set of heatsink structures.

15. A wearable cooling system comprising:

a garment insert, integrated into a garment, configured to be worn across a dermal surface, and comprising:

a textile panel defining:

an inner surface configured to contact the dermal surface;

an outer surface opposite the inner surface; and a first grid receptacle extending between the inner surface and the outer surface; and a first grid structure:

rigidly arranged within and spanning the first grid receptacle;

formed of a flexible material; and defining:

an inner face facing the inner surface of the textile panel;

an outer face opposite the inner face and facing the outer surface of the textile panel; and a grid array of apertures arranged in a first pattern coplanar the first grid receptacle; and a first cooling unit:

configured to transiently mate with a grid structure, in the set of grid structures, to seat within a corresponding grid receptacle in the set of grid receptacles;

comprising a first heatsink structure:
formed of a rigid material comprising a porous structure;
defining:
a base section defining:
an interior surface configured to contact the dermal surface; and
an outer base surface configured to seat against the inner face of the grid structure; and
a set of heatsink columns:
extending from the outer base surface;
arranged in a second pattern complementary to the first pattern; and
configured to seat extending through the corresponding grid array of apertures to transiently retain the cooling unit within the grid receptacle abutting surfaces of the grid structure; and
configured to wick moisture through the porous structure from the dermal surface toward surfaces of the set of heatsink columns; and
comprising a first polymer frame:
rigidly coupled to the first heatsink structure and arranged about the base section; and
configured to abut surfaces of the base section to surfaces of the first grid receptacle to flexibly retain the first cooling unit within the first grid receptacle in an assembled configuration.

16. The wearable cooling system of claim 15:
wherein the first grid receptacle is formed of a silicone material configured to contour about the dermal surface;
wherein the first heatsink structure comprises:
a substrate:
formed of a conductive material;
defining the base section and the set of heatsink columns defining an exterior surface of the heatsink structure; and
defining an open network of pores extending between the interior surface and the exterior surface; and
a coating:
formed of a porous, hydrophilic material;
extending across the interior surface of the substrate;
lining the open network of pores;
defining a void network configured to filter hydrophobic molecules; and
configured to cooperate with the substrate to wick moisture from the dermal surface, through the void network lining the open network of pores, and to the exterior surface, to cool the dermal surface; and
wherein the polymer frame is formed of a polymer material exhibiting a target flexibility.

17. The wearable cooling system of claim 15:
wherein the textile panel defines a second grid receptacle extending between the inner surface and the outer surface;
wherein the garment insert comprises a second grid structure:
arranged within and spanning the second grid receptacle; and
defining:
a second inner face facing the inner surface of the textile panel and coplanar the inner face;
a second outer face opposite the second inner face and facing the outer surface of the textile panel; and
a second grid array of apertures arranged in the first pattern and coplanar the second grid receptacle;
further comprising a second cooling unit comprising:
a second heatsink structure:
defining:
a second base section defining:
o a second interior surface configured to contact the dermal surface; and
a second outer base surface opposite the second interior surface; and
a second set of heatsink columns:
extending from the second outer base surface;
arranged in the second pattern corresponding complementary to the first pattern; and
each heatsink column, in the second set of heatsink columns, configured to seat extending through an aperture, in the second grid array of apertures; and
configured to wick moisture from the dermal surface toward surfaces of the second set of heatsink columns; and
a second polymer frame:
rigidly coupled to the second heatsink structure and arranged about the second base section; and
configured to abut surfaces of the second base section to surfaces of the second grid receptacle to flexibly retain the second cooling unit within the second grid receptacle in the assembled configuration.

18. The wearable cooling system of claim 15:
wherein the first cooling unit is configured to mate with the first grid structure to seat within the first grid receptacle during a first time period; and
further comprising a second cooling unit comprising:
a second heatsink structure:
defining:
a second base section:
defining an inner surface configured to contact the dermal surface; and
a second outer base surface opposite the second interior surface; and
a second set of heatsink columns:
extending from the second outer base surface;
arranged in the second pattern complementary to the first pattern; and
configured to seat extending through the grid array of apertures;
configured to wick moisture from the dermal surface toward surfaces of the set of heatsink columns; and
configured to mate with the first grid structure to seat within the first grid receptacle during a second time period succeeding the first time period; and
a second polymer frame:
rigidly coupled to the second heatsink structure and arranged about the second base section; and
configured to abut surfaces of the second base section to surfaces of the second grid receptacle to flexibly retain the second cooling unit within the second grid receptacle in the assembled configuration.

19. A wearable cooling system comprising:

a garment insert configured to be worn across a dermal surface and comprising:

a textile panel defining:

an inner surface configured to contact the dermal surface;

an outer surface opposite the inner surface; and a grid receptacle extending between the inner surface and the outer surface; and a grid structure:

rigidly arranged within and spanning the grid receptacle;

formed of a first flexible material; and defining:

an inner face facing the inner surface of the textile panel;

an outer face opposite the inner face and facing the outer surface of the textile panel; and a grid array of apertures arranged in a first pattern coplanar the grid receptacle; and a cooling unit:

configured to transiently mate with a grid structure, in the set of grid structures, to seat within a corresponding grid receptacle, in the set of grid receptacles, defining a corresponding grid array of apertures;

a heatsink structure:

formed of a rigid material;

comprising a substrate defining:

a base section defining an interior surface configured to contact the dermal surface and an outer base surface opposite the interior surface;

a set of heatsink columns:

extending from the outer base surface of the base section;

defining an exterior surface;

arranged in a second pattern complementary to the first pattern; and configured to seat extending through the corresponding grid array of apertures to transiently retain the cooling unit within the grid receptacle in an assembled configuration; and an open network of pores extending between the interior surface of the base section and the exterior surface of the set of heatsink columns; and comprising a coating:

formed of a hydrophilic material;

extending across the interior surface of the substrate and lining the open network of pores;

defining a void network; and configured to cooperate with the substrate to wick moisture from the dermal surface, through the void network lining the open network of pores, and to the exterior surface, to cool the dermal surface; and a polymer frame:

formed of a flexible material;

rigidly coupled to the heatsink structure and arranged about the base section; and configured to abut surfaces of the base section to surfaces of the grid receptacle to flexibly retain the cooling unit within the grid receptacle in the assembled configuration.

20. The wearable cooling system of claim 19:

wherein the textile panel defines a second grid receptacle extending between the inner surface and the outer surface;

wherein the garment insert is integrated into a garment and comprises a second grid structure:

arranged within and spanning the second grid receptacle; and defining:

a second inner face facing the inner surface of the textile panel;

a second outer face opposite the second inner face and facing the outer surface of the textile panel; and a second grid array of apertures arranged in the first pattern coplanar the second grid receptacle; and a second cooling unit comprising:

a second heatsink structure comprising:

a second substrate defining:

a second base section defining a second interior surface configured to contact the dermal surface;

a second set of heatsink columns:

extending from the second base section opposite the second interior surface;

defining a second exterior surface;

arranged in the second pattern corresponding to the first pattern; and configured to seat extending through the second grid array of apertures in the assembled configuration; and a second open network of pores extending between the second interior surface and the second exterior surface; and a second coating:

formed of the hydrophilic material;

extending across the second interior surface of the second substrate and lining the second open network of pores;

defining a second void network; and configured to cooperate with the second substrate to wick moisture from the dermal surface, through the second void network lining the second open network of pores, and to the second exterior surface, to cool the dermal surface; and a second polymer frame:

rigidly coupled to the second heatsink structure and arranged about the second base section; and configured to abut surfaces of the second base section to surfaces of the second grid receptacle to flexibly retain the second cooling unit within the second grid receptacle in the assembled configuration.

* * * * *